US008597911B2

(12) United States Patent
Miyazaki et al.

(10) Patent No.: US 8,597,911 B2
(45) Date of Patent: Dec. 3, 2013

(54) PROCESS FOR PRODUCING ANTIBODIES

(75) Inventors: Taro Miyazaki, Shizuoka (JP); Tetsuo Kojima, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/560,098

(22) PCT Filed: Jun. 11, 2004

(86) PCT No.: PCT/JP2004/008585
§ 371 (c)(1),
(2), (4) Date: Apr. 28, 2006

(87) PCT Pub. No.: WO2004/111233
PCT Pub. Date: Dec. 23, 2004

(65) Prior Publication Data
US 2006/0269989 A1 Nov. 30, 2006

(30) Foreign Application Priority Data

Jun. 11, 2003 (JP) .................................. 2003-167087
Nov. 4, 2003 (WO) ........................ PCT/JP03/14059

(51) Int. Cl.
*C12N 15/13* (2006.01)
(52) U.S. Cl.
USPC ........................................................ 435/69.7
(58) Field of Classification Search
None
See application file for complete search history.

(56) References Cited

U.S. PATENT DOCUMENTS

| 5,837,821 | A | 11/1998 | Wu |
| 5,877,291 | A | 3/1999 | Mezes et al. |
| 5,945,311 | A | 8/1999 | Lindhofer et al. |
| 6,126,980 | A | 10/2000 | Smith et al. |
| 6,132,992 | A | 10/2000 | Ledbetter et al. |
| 6,183,744 | B1 | 2/2001 | Goldenberg |
| 6,323,000 | B2 | 11/2001 | Briggs et al. |
| 6,342,220 | B1 | 1/2002 | Adams et al. |
| 6,368,596 | B1 | 4/2002 | Ghetie et al. |
| 6,683,157 | B2 | 1/2004 | Briggs et al. |
| 6,699,686 | B1 | 3/2004 | Brocard et al. |
| 8,062,635 | B2 * | 11/2011 | Hattori et al. ............. 424/136.1 |
| 2002/0142374 | A1 | 10/2002 | Gallo et al. |
| 2002/0155537 | A1 | 10/2002 | Carter et al. |
| 2002/0164668 | A1 | 11/2002 | Durham et al. |
| 2003/0224397 | A1 | 12/2003 | Lowman et al. |
| 2004/0091475 | A1 | 5/2004 | Tsuchiya et al. |
| 2004/0219643 | A1 | 11/2004 | Winter et al. |
| 2005/0130224 | A1 | 6/2005 | Saito et al. |
| 2005/0191293 | A1 | 9/2005 | Deshpande et al. |
| 2005/0266425 | A1 | 12/2005 | Zauderer et al. |
| 2006/0058511 | A1 | 3/2006 | Tanikawa et al. |
| 2006/0159673 | A1 | 7/2006 | Kojima |
| 2006/0160184 | A1 | 7/2006 | Hoogenboom et al. |
| 2006/0204493 | A1 | 9/2006 | Huang et al. |
| 2006/0222643 | A1 | 10/2006 | Tsunoda et al. |
| 2007/0003556 | A1 | 1/2007 | Tsuchiya et al. |
| 2007/0041978 | A1 | 2/2007 | Hattori et al. |
| 2007/0087381 | A1 | 4/2007 | Kojima |
| 2007/0281327 | A1 | 12/2007 | Nakano et al. |
| 2008/0009038 | A1 | 1/2008 | Ohtomo et al. |
| 2008/0075712 | A1 | 3/2008 | Hattori et al. |
| 2008/0206229 | A1 | 8/2008 | Ono et al. |
| 2009/0028854 | A1 | 1/2009 | Igawa et al. |
| 2009/0117097 | A1 | 5/2009 | Igawa et al. |
| 2009/0214535 | A1 | 8/2009 | Igawa et al. |
| 2009/0263392 | A1 | 10/2009 | Igawa et al. |
| 2009/0297501 | A1 | 12/2009 | Igawa et al. |
| 2010/0003254 | A1 | 1/2010 | Hattori et al. |
| 2010/0015133 | A1 | 1/2010 | Igawa et al. |
| 2010/0291072 | A1 | 11/2010 | Lowman et al. |
| 2011/0076275 | A1 | 3/2011 | Igawa et al. |
| 2011/0236374 | A1 | 9/2011 | Shitara et al. |
| 2012/0237517 | A1 | 9/2012 | Hattori et al. |
| 2013/0018174 | A1 | 1/2013 | Igawa et al. |

FOREIGN PATENT DOCUMENTS

| CA | 2 331 641 | 11/1999 |
| CA | 2603264 | 10/2006 |
| DE | 198 19 846 | 11/1999 |
| EP | 0 774 511 | 5/1997 |
| EP | 811 691 | 12/1997 |
| EP | 1 327 681 | 7/2003 |
| EP | 1510943 | 3/2005 |
| EP | 1693448 | 8/2006 |
| EP | 1870459 | 12/2007 |
| EP | 2 107 115 | 10/2009 |
| JP | 8-500979 | 2/1996 |

(Continued)

OTHER PUBLICATIONS

Hozumi, N. & Tonegawa, S. Proc. Natl. Acad. Sci. U.S.A. 73, 3628-3632 (1976).*
Sinha et al. (2005) Cell Biochem Biophys 43:253-273.*
Arndt et al. (2001) J Mol Biol 312: 221-228.*
Smith (The Scientist Magazine, Feb. 2, 1998, pp. 1-3).*
Life Technologies (Invitrogen; "ecdysone analogue" and pIND plasmid; pp. 1-2; Aug. 10, 2012).*
Cekaite et al., "Protein Arrays: A Versatile Toolbox for Target Identification and Monitoring of Patient Immune Responses," Methods Mol. Biol., 360:335-348 (2007).
Andris-Widhopf et al., "Methods for the generation of chicken monoclonal antibody fragments by phage display," *J. Immunol. Methods*, 242:159-181 (2000).

(Continued)

*Primary Examiner* — Brad Duffy
*Assistant Examiner* — Nelson B Moseley, II
(74) *Attorney, Agent, or Firm* — Fish & Richardson P.C.

(57) ABSTRACT

Focusing on the fact that antibody molecules with one H chain are not secreted when using the "knobs-into-holes" method, the present inventors revealed that desired bispecific antibodies can be preferentially formed by first expressing the H and L chains of one arm, and then suppressing their expression, followed by expressing the H and L chains of the other arm so that first desired HL molecules (HaLa and HbLb) are constructed, and then the H chains are paired with each other ($H_2L_2$). The present invention was thus completed.

14 Claims, 2 Drawing Sheets

(56) References Cited

FOREIGN PATENT DOCUMENTS

| | | |
|---|---|---|
| JP | 09506001 | 6/1997 |
| JP | 11-500915 | 1/1999 |
| JP | 11-500916 | 1/1999 |
| JP | 2001-523971 | 11/2001 |
| JP | 2002-543822 | 12/2002 |
| JP | 2003-515323 | 5/2003 |
| JP | 2004-086682 | 3/2004 |
| JP | 2005/537009 | 12/2005 |
| WO | WO 94/05690 | 3/1994 |
| WO | WO9533844 | 12/1995 |
| WO | WO9601653 A1 | 1/1996 |
| WO | WO 96/27011 | 9/1996 |
| WO | WO 96/34892 | 11/1996 |
| WO | WO 97/10354 | 3/1997 |
| WO | WO9803546 | 1/1998 |
| WO | WO 98/50431 | 11/1998 |
| WO | WO 99/03495 | 1/1999 |
| WO | WO 00/44788 | 8/2000 |
| WO | WO 00/69462 | 11/2000 |
| WO | WO 01/36486 | 5/2001 |
| WO | WO 01/44282 | 6/2001 |
| WO | WO 01/70775 | 9/2001 |
| WO | WO 01/79494 | 10/2001 |
| WO | WO 02/33072 | 4/2002 |
| WO | WO 02/33073 | 4/2002 |
| WO | WO 03/087163 | 10/2003 |
| WO | WO 2004/019966 | 3/2004 |
| WO | WO 2004/020579 | 3/2004 |
| WO | WO 2004/111233 | 12/2004 |
| WO | WO2005035756 A1 | 4/2005 |
| WO | WO 2005/056604 | 6/2005 |
| WO | WO 2005/107784 | 11/2005 |
| WO | WO 2006/106905 | 10/2006 |
| WO | WO 2006/109592 | 10/2006 |
| WO | WO2006106903 A1 | 10/2006 |
| WO | WO2006106905 | 10/2006 |
| WO | WO 2007/114325 | 10/2007 |
| WO | WO 2008/090960 | 7/2008 |
| WO | WO 2010/051792 | 5/2010 |

OTHER PUBLICATIONS

De Jonge et al., "Production and Characterization of Bispecific Single-Chain Antibody Fragments," *Mol. Immunol.*, 32:1405-1412 (1995).

DeNardo et al., "Anti-HLA-DR/anti-DOTA Diabody Construction in a Modular Gene Design Platform: Bispecific Antibodies for Pretargeted Radioimmunotherapy," *Cancer Biother. Radiopharm.*, 16:525-535 (2001).

Goldstein et al., "Cytolytic and Cytostatic Properties of an Anti-Human FcγRI (CD64) × Epidermal Growth Factor Bispecific Fusion Protein," *J. Immunol.*, 158:872-879 (1997).

Holliger et al., "Diabodies: Small bivalent and bispecific antibody fragments," *Proc. Natl. Acad. Sci. USA*, 90:6444-6448 (1993).

Hoogenboom et al., "Multi-subunit proteins on the surface of filamentous phage: methodologies for displaying antibody (Fab) heavy and light chains," *Nucleic Acids Res.*, 19:4133-4137 (1991).

Hudson et al., "High avidity scFv multimers; diabodies and triabodies," *J. Immunol. Methods*, 231:177-189 (1999).

Kipriyanov et al., "Effect of Domain Order on the Activity of Bacterially Produced Bispecific Single-chain Fv Antibodies," *J. Mol. Biol.*, 330:99-111 (2003).

Krebber et al., "Reliable cloning of functional antibody variable domains from hybridomas and spleen cell repertoires employing a reengineered phage display system," *J. Immunol. Methods*, 201:35-55 (1997).

Kurucz et al., "Retargeting of CTL by an Efficiently Refolded Bispecific Single-Chain Fv Dimer Produced in Bacteria," *J. Immunol.*, 154:4576-4582 (1995).

Little et al., "Of mice and men: hybridoma and recombinant antibodies," *Immunol. Today*, 21:364-370 (2000).

McGuinness et al., "Phage diabody repertoires for selection of large numbers of bispecific antibody fragments," *Nat. Biotechnol.*, 14:1149-1154 (1996).

Merchant et al., "An efficient route to human bispecific IgG," *Nat. Biotechnol.*, 16:677-681 (1998).

Plückthun et al., "New protein engineering approaches to multivalent and bispecific antibody fragments," *Immunotechnology*, 3:83-105 (1997).

Tang et al., "Selection of Linkers for a Catalytic Single-chain Antibody Using Phage Display Technology," *J. Biol. Chem.*, 271:15682-15686 (1996).

Turner et al., "Importance of the linker in expression of single-chain Fv antibody fragments: optimisation of peptide sequence using phage display technology," *J. Immunol. Methods*, 205:43-54 (1997).

Vökel et al., "Optimized linker sequences for the expression of monomeric and dimeric bispecific single-chain diabodies," *Protein Eng.*, 14:815-823 (2001).

Carter, "Bispecific human IgG by design", J. Immunol. Methods, 248:7-15 (2001).

Peipp et al., "Bispecific antibodies targeting cancer cells", Biochem. Soc. Trans., 30:507-11 (2002).

Ridgway et al., "'Knobs-into-holes' engineering of antibody CH3 domains for heavy chain heterodimerization", Protein Engineering 9:617-621 (1996).

Shalaby et al., "Development of Humanized Bispecific Antibodies Reactive with Cytotoxic Lymphocytes and Tumor Cells Overexpressing the HER2 Protooncogene", J. Exp. Med.; 175:217-225 (1992).

Skerra, "Use of the tetracycline promoter for the tightly regulated production of a murine antibody fragment in *Escherichia coli*", Gene, 151:131-5 (1994).

Zuo et al., "An efficient route to the production of an IgG-like bispecific antibody", Protein Engineering 13:361-367 (2000).

Casset et al., "A peptide mimetic of an anti-CD4 monoclonal antibody by rational design", Biochemical and Biophysical Research Communications 307:198-205, 2003.

Chen et al., "Selection and analysis of an optimized anti-VEGF antibody: crystal structure of an affinity-matured fab in complex with antigen", J. Mol. Biol. 293:865-881, 1999.

Holm et al., "Functional mapping and single chain construction of the anti-cytokeratin 8 monoclonal antibody TS1", Molecular Immunology 44:1075-1084, 2007.

Kumar et al., "Molecular cloning and expression of the fabs of human autoantibodies in *Escherichia coli*", The Journal of Biological Chemistry 276(41):33129-33136, 2000.

MacCullum et al., "Antibody-antigen interactions: contact analysis and binding site topography", J. Mol. Biol. 262:732-745, 1996.

Pascalis et al., "Grafting of "abbreviated" complementarity-determining regions containing specificity-determining residues essential for ligand contact to engineer a less immunogenic humanized monoclonal antibody", The Journal of Immunology 169:3076-3084, 2002.

Smith-Gill et al., "Contributions of immunoglobulin heavy and light chains to antibody specificity for lysozyme and two haptens", The Journal of Immunology 139:4135-4144, 1997.

Song et al., "Light chain of natural antibody plays a dominant role in protein antigen binding", Biochemical and Biophysical Research Communications 268:390-394, 2000.

Vajdos et al., "Comprehensive functional maps of the antigen-binding site of an anti-ErbB2 antibody obtained with shotgun scanning mutagenesis", J. Mol. Biol. 320:415-428, 2002.

Wu et al., "Humanization of a murine monoclonal antibody by simultaneous optimization of framework and CDR residues", J. Mol. Biol. 294:151-162, 1999.

U.S. Appl. No. 11/910,117, filed Aug. 2007, Igawa et al.

U.S. Appl. No. 11/910,128, filed Sep. 2007, Igawa et al.

U.S. Appl. No. 11/916,979, filed Aug. 2008, Igawa.

Arndt et al., "Generation of a highly stable, internalizing anti-DC22 single-chain Fv fragment for targeting non-Hodgkin's lymphoma," *Int. J. Cancer*, 107(5):822-829 (2003).

Bowie et al., "Deciphering the Message in Protein Sequences: Tolerance to Amino Acid Substitutions," *Science*, 247:1306-1310 (1990).

Clackson et al., "Making antibody fragments using phage display libraries," *Nature*, 352:624-628 (1991).

(56) References Cited

OTHER PUBLICATIONS

Cochlovius et al., "Treatment of human B cell lymphoma xenografts with a CD3 × CD19 diabody and T cells", The Journal of Immunology 165:888-895 (2000).

Dejonge et al., "In vivo retargeting of T cell effector function by recombinant bispecific single chain Fv (anti-DC3 × anti-idiottype) induces long term survival of the murine BCL1 lymphoma model," *J. Immunol.*, 161(3):1454-1461 (1998).

Desplancq et al., "Multimerization behaviour of single chain Fv variants for the tumour-binding antibody B72.3," *Protein Engineering*, 7(8):1027-1033 (1994).

Eijsink et al., "Rational engineering of enzyme stability," *Journal of Biotechnology*, 113:105-120 (2004).

Ewert et al., "Biophysical properties of human antibody variable domains," *J. Mol. Biol.*, 325:531-553 (2003).

Ewert et al., "Stability improvement of antibodies for extracellular and intracellular applications: CDR grafting to stable frameworks and structure-based framework engineering," *Methods*, 34:184-199 (2004).

Ewert et al., "Structure-based improvement of the biophysical properties of immunoglobulin $V_H$ domains with a generalizable approach," *Biochemistry*, 42:1517-1528 (2003).

Gruber et al., "Efficient tumor cell lysis mediated by a bispecific single chain antibody expressed in *Escherichia coli*," *Journal of Immunology*, 152:5368-5374 (1994).

Jäger et al., "Folding and assembly of an antibody Fv fragment, a heterodimer stabilized by antigen," *Journal of Molecular Biology*, 285:2005-2019 (1999).

Kipriyanov and Little, "Generation of Recombinant Antibodies," *Molecular Biotechnology*, 12:173-201 (1999).

Kipriyanov et al., "Bispecific CD3 × CD19 diabody for T cell-mediated lysis of malignant human B cells," *In. J. Cancer*, 77:763-772 (1998).

Kipriyanov et al., "Bispecific tandem diabody for tumor therapy with imprived antigen binding and pharmacokinetics," *Journal of Molecular Biology*, 293:41-56 (1999).

Korn et al., "Recombinant bispecific antibodies for the targeting of adenoviruses to CEA-expressing tumour cells: a comparative analysis of bacterially expressed single-chain diabody and tandem scFv," *The Journal of Gene Medicine*, 6:642-651 (2004).

Kriangkum et al., "Bispecific and bifunctional single chain recombinant antibodies," *Biomol. Eng.*, 18(2):31-40 (2001).

Kumar et al., "The second PDZ domain of INAD is a type I domain involved in binding to eye protein kinase C. Mutational analysis and naturally occuring variants," *J. Biol. Chem.*, 276(27):24971-24977 (2001).

Le Gall et al., "Effect of linker sequences between the antibody variable domains on the formation, stability and biological activity of a bispecific tandem diabody," *Protein Engineering Design & Selection*, 17(4):357-366 (2004).

Liu et al., "Functional interactions between arginine-133 and aspartate-88 in the human reduced folate carrier: evidence for a charge-pair association," *Biochem. J.*, 358:511-516 (2001).

Mack et al., "A small bispecific antibody construct expressed as a functional single-chain molecule with high tumor cell cytotoxicity," *Proc. Natl. Acad. Sci. USA*, 92(15):7021-7025 (1995).

Maity et al., "Equilibrium unfolding of dimeric and engineered monomeric forms of Cro (F58W) repressor and the effect of added salts: evidence for the formation of folded monomer induced by sodium perchlorate," *Archives of Biochemistry and Biophysics*, 434:93-107 (2005).

Mallender et al., "Construction, expression and activity of a bivalent bispecific single-chain antibody," *J. Biol. Chem.*, 269(1):199-206 (1994).

Meng et al., "The evaluation of recombinant, chimeric, tetravalent antihuman CD22 antibodies," *Clinical Cancer Research*, 10:1274-1281 (2004).

Ngo et al., "Computational Complexity, Protein Structure Prediction, and the Levinthal Paradox," *The Protein Folding Problem and Tertiary Structure Prediction*, Merz, Jr. et al. Editors, Birkhauser Boston, 433-506 (1994).

Nieba et al., "Disrupting the hydrophobic patches at the antibody variable/constant domain interface: improved in vivo folding and physical characterization of an engineered scFv fragment," *Protein Engineering*, 10(4):435-444 (1997).

Nishii, "CD22 antibody therapy," *Current Therapy*, 20:47-50 (2001) (English translation included).

Nohaile et al., "Altering dimerization specificity by changes in surface electrostatics," *PNAS* 98(6):3109-3114 (2001).

Orita et al., "A novel therapeutic approach for thrombocytopenia by minibody agonist of the thrombopoietin receptor," Blood, 105:562-566 (2005).

Rajagopal et al., "A form of anti-Tac (Fv) which is both single-chain and disulfide stabilized: comparison with its single-chain and disulfide-stabilized homologs," *Protein Engineering*, 10(12):1453-1459 (1997).

Rousch et al., "Somatostatin displayed on filamentous phage as a receptor-specific agonist," *Br. J. Pharmacol.*, 125:5-16 (1998).

Sal-Man et al., "Arginine mutations within a transmembrane domain of Tar, an *Escherichia coli* aspartate receptor, can drive monodimer dissociation and heterodimer association n. vivo," *Biochem. J.*, 385(1):29-36 (2005).

Segal et al., "Bispecific antibodies in cancer therapy," *Current Opinion in Immunology*, 11:558-582 (1999).

Shimba et al., "Comparative thermodynamic analyses of the Fv, Fab* and Fab fragments of anti-dansyl mouse monoclonal antibody," *FEBS Letters*, 360:247-250 (1995).

Shire et al., "Challenges in the development of high protein concentration formulations," *Journal of Pharmaceutical Sciences*, 93(6):1390-1402 (2004).

Tan et al., "Contributions of a highly conserved $V_H/V_L$ hydrogen bonding interaction to scFv folding stability and refolding efficiency," *Biophysical Journal*, 75:1473-1482 (1998).

Van Den Burg et al., "Selection of mutations for increased protein stability," *Curr. Opin. Biotechnol.*, 13(4):333-337 (2002).

Vieille et al., "Hyperthermophilic enzymes: sources, uses, and molecular mechanisms for thermostability," *Microbiology and Molecular Biology Reviews*, 65(1):1-43 (2001).

Wells, "Perspectives in Biochemistry," *Biochemistry*, 29(37):8509-8517 (1990).

Whitlow et al., "An improved linker for single-chain Fv with reduced aggregation and enhanced proteolytic stability," *Protein Engineering*, 6(8):989-995 (1993).

Worn et al., "Stability engineering of antibody single-chain Fv fragments," *J. Mol. Biol.*, 305:989-1010 (2001).

Zhu et al., "Remodeling domain interfaces to enhance heterodimer formation," *Protein Science*, 6:781-788 (1997).

USPTO Restriction Requirement in U.S. Appl. No. 10/551,504, mailed Jun. 27, 2008, 6 pages.

Fish & Richardson P.C., Response to Restriction Requirement dated Jun. 27, 2008 in U.S. Appl. No. 10/551,504, filed Sep. 29, 2008, 13 pages.

USPTO Restriction Requirement in U.S. Appl. No. 10/551,504, mailed Dec. 16, 2008, 5 pages.

Fish & Richardson P.C., Response to Restriction Requirement dated Dec. 16, 2008 in U.S. Appl. No. 10/551,504, filed Dec. 23, 2008, 14 pages.

USPTO Non-Final Office Action in U.S. Appl. No. 10/551,504, mailed Apr. 15, 2009, 35 pages.

Japanese Patent Office, International Search Report for U.S. Appl. No. PCT/JP2004/018506, mailed Mar. 22, 2005, 3 pages.

International Preliminary Report on Patentability for App. Ser. No. PCT/JP2004/018506, 8 pages.

European Search Report for App. Ser. No. EP 04 82 0316, dated Jul. 17, 2008, 3 pages.

Japanese Patent Office, International Search Report for App. Ser. No. PCT/JP2006/306800, mailed May 16, 2006, 4 pages.

International Preliminary Report on Patentability for App. Ser. No. PCT/JP2006/306800, dated Oct. 3, 2007, 6 pages.

(56) References Cited

OTHER PUBLICATIONS

Japanese Patent Office, International Search Report for App. Ser. No. PCT/US2006/306803, mailed Jul. 11, 2006, 4 pages.
International Preliminary Report on Patentability for App. Ser. No. PCT/US2006/306803, dated Oct. 3, 2007, 6 pages.
Japanese Patent Office, International Search Report for App. Ser. No. PCT/JP2006/311575, mailed Sep. 26, 2006, 3 pages.
International Preliminary Report on Patentability for App. Ser. No. PCT/JP2006/311575, dated Dec. 11, 2007, 5 pages.
Japanese Patent Office, International Search Report for App. Ser. No. PCT/JP2006/311600, mailed Aug. 29, 2006, 2 pages.
International Preliminary Report on Patentability for App. Ser. No. PCT/JP2006/31160, dated Dec. 11, 2007, 8 pages.
Abe et al., "Surrogate thrombopoietin," *Immunology Letters*, 61:73-78 (1998).
Creighton, "Protein folding," *Biochem. J.*, 270(1):1-16 (1990).
Deng et al., "An Agonist Murine Monoclonal Antibody to the Human c-Mpl Receptor Stimulates Megakaryocytopoiesis," *Blood*, 92:1981-1988 (1998).
Elliott et al., "Activation of the Erythropoietin (EPO) Receptor by Bivalent Anti-EPO Receptor Antibodies," *J. Biol. Chem.*, 271:24691-24697 (1996).
Goding, "Monoclonal Antibodies: Principles and Practice," *Academic Press*, second Ed., 125:129 (1986).
Kontermann, R., "Recombinant bispecific antibodies for cancer therapy," *Acta Pharmacol. Sin.*, 26(1):1-9 (2005).
Palacios et al., "IL-3-dependent mouse clones that express B-220 surface antigen, contain Ig genes in germ-line configuration, and generate B Lymphocutes in vivo," *Cell*, 41:727-734 (1985).
Souyri, "Mpl: from an acute myeloproliferative virus to the isolation of the long sought thrombopoietin," *Seminars in Hematology*, 35(3):222-231 (1998).
Fish & Richardson P.C., Amendment in Reply to Action dated Apr. 15, 2009 in U.S. Appl. No. 10/551,504, filed Aug. 14, 2009, 19 pages.
International Search Report for App. Ser. No. PCT/JP2004/008585, mailed Sep. 7, 2004, 4 pages.
International Preliminary Report on Patentability for App. Ser. No. PCT/JP2004/008585, 10 pages.
European Search Report for App. Ser. No. EP 06 73 0748, dated Apr. 22, 2009, 7 pages.
USPTO Notice of Allowance in U.S. Appl. No. 10/551,504, mailed Jan. 7, 2010, 13 pages.
Moore et al., "Kinetics and thermodynamics of dimer formation and dissociation for a recombinant humanized monoclonal antibody to vascular endothelial growth factor," Biochemistry, 38:13960-13967 (1999).
European Search Report for App. Ser. No. EP 06 76 6512, dated Nov. 30, 2009, 6 pages.
USPTO Restriction Requirement in U.S. Appl. No. 11/910,117, mailed May 3, 2010, 9 pages.
Blazar, "Infusion of Anti-B7.1 (CD80) and Anti-B7.2 (CD86) Monoclonal Antibodies Inhibits Murine Graft-Versus-Host Disease Lethality in Part Via Direct Effects on CD4+ and CD8+ T Cells," J. Immunol., 157:3250-59 (1996).
Schmidt et al., Human Physiology, Moscow, 2:431-436 (1996), and English translation: Schmidt et al., "Hemostatis and Coagulation," Human Physiology, R.F. Schmidt, G. Thews (Eds), Second, Completely Revised Edition, 418-423 [translated by Marguerite A. Biederman-Thorson], Springer-Verlag, 1989.
Schmidt et al., Human Physiology, Moscow, 3:764 (1996), and English translation: Schmidt et al., "Enzymes of the pancreatic juice," Human Physiology, R.F. Schmidt, G. Thews (Eds.), Second, Completely Revised Edition, 716 [translated by Marguerite A. Biederman-Thorson], Springer-Verlag, 1989.
Fish & Richardson P.C., Amendment and Response to Restriction Requirement dated Nov. 18, 2009 in U.S. Appl. No. 10/575,905, filed Apr. 16, 2010, 12 pages.
Fish & Richardson P.C., Amendment in Reply to Action dated Jun. 23, 2010 in U.S. Appl. No. 10/575,905, filed Dec. 22, 2010, 10 pages.
Fish & Richardson P.C., Amendment in Reply to Action dated Jun. 23, 2010 in U.S. Appl. No. 10/575,193, filed Dec. 22, 2010, 13 pages.
Adams et al., "Humanization of a recombinant monoclonal antibody to produce a therapeutic HER dimerization inhibitor, pertuzumab," Cancer Immunol. Immunother., 55:717-727 (2006).
Binz et al., "Engineering novel binding proteins from nonimmunoglobulin domains," Nat. Biotechnol., 23:1257-68 (2005).
Branden and Tooze, "Recognition of Foreign Molecules by the Immune System," Introduction to Protein Structure, 2d Ed., Garland Publishing, pp. 299-323 (1999).
Comper and Glasgow, "Charge selectivity in kidney ultrafiltration," Kidney Int, 47:1242-51 (1995).
Couto et al., "Anti-BA46 Monoclonal Antibody Mc3: Humanization Using a Novel Positional Consensus and in Vivo and in Vitro Characterization," Cancer Research, 55:1717-1722 (1995).
Deen et al., "Structural determinants of glomerular permeability," Am. J. Physiol. Renal. Physiol., 281:F579-F596 (2001).
Del Rio et al., "An Engineered Penicillin Acylase with Altered Surface Charge Is More Stable in Alkaline pH," Ann. NY Acad. Sci., 799:61-64 (1996).
Ghetie and Ward, "FcRn: the MHC class I-related receptor that is more than an IgG transporter," Immunol. Today, 18:592-598 (1997).
Ghetie et al., "Increasing the serum persistence of an IgG fragment by random mutagenesis," Nature Biotechnology, 15:637-640 (1997).
Ghetie et al., "Multiple roles for the major histocompatibility complex class I-related receptor FcRn," Annu. Rev. Immunol., 18:739-766 (2000).
Gobburu et al., "Pharmacokinetics/dynamics of 5c8, a monoclonal antibody to CD154 (CD40 ligand) suppression of an immune response in monkeys," J. Pharmacol. Exp. Ther., 286:925-930 (1998).
Goode et al., "The glomerular basement membrane charge-selectivity barrier: an oversimplified concept?," Nephrol. Dial. Transplant., 11:1714-16 (1996).
Graves et al., "Molecular modeling and preclinical evaluation of the humanized NR-LU-13 antibody," Clin. Cancer Res., 5:899-908 (1999).
Gupta et al., "Affinity chromatography and co-chromatography of bispecific monoclonal antibody immunoconjugates," J. Biochem. Biophys. Methods, 51:203-216 (2002).
He et al., "Humanization and pharmacokinetics of a monoclonal antibody with specificity for both E- and P-selectin," J. Immunol., 160:1029-35 (1998).
Hinton et al., "An engineered human IgG1 antibody with longer serum half-life," J. Immunol., 176:346-356 (2006).
Kashmiri et al., "Generation, characterization, and in vivo studies of humanized anticarcinoma antibody CC49," Hybridoma, 14:461-473 (1995).
Khawli et al., "Improved tumor localization and radioimaging with chemically modified monoclonal antibodies," Cancer Biother. Radiopharm., 11:203-215 (1996).
Kim et al., "Antibody Engineering for the Development of Therapeutic Antibodies," Mol. Cells, 20:17-29 (2005).
Kim et al., "Chemical modification to reduce renal uptake of disulfide-bonded variable region fragment of anti-tac monoclonal antibody labeled with 99mTc," Bioconjugate Chem., 10:447-453 (1999).
Kim et al., "Lowering of pI by acylation improves the renal uptake of 99mTc-labeled anti-Tac dsFv: effect of different acylating reagents," Nucl. Med. Biol., 29:795-801 (2002).
Kobayashi et al., "The pharmacokinetic characteristics of glycolated humanized anti-Tac Fabs are determined by their isoelectric points," Cancer Res., 59:422-430 (1999).
Kreutz et al., "Efficient bispecific monoclonal antibody purification using gradient thiophilic affinity chromatography," J. Chromatogr. B, 714:161-170 (1998).
Lindhofer et al., "Preferential Species-Restricted Heavy/Light Chain Pairing in Rat/Mouse Quadromas," J. Immunol., 155:219-225 (1995).
Lobo et al., "Antibody pharmacokinetics and pharmacodynamics," J. Pharm. Sci., 93:2645-68 (2004).

(56) References Cited

OTHER PUBLICATIONS

Manzke et al., "Single-step purification of bispecific monoclonal antibodies for immunotherapeutic use by hydrophobic interaction chromatography," J. Immunol. Methods, 208:65-73 (1997).
Martin et al- "Crystal structure at 2.8 A of an FcRn/heterodimeric Fc complex: mechanism of pH-dependent binding," Mol. Cell, 7:867-877 (2001).
Marvin et al., "Recombinant approaches to IgG-like bispecific antibodies," Acta. Pharmacol. Sin., 26:649-658 (2005).
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Pavlinkova et al., "Charge-modified single chain antibody constructs of monoclonal antibody CC49: Generation, characterization, pharmacokinetics, and biodistribution analysis," Nucl. Med. Biol., 26:27-34 (1999).
Pavlou et al., "The therapeutic antibodies market to 2008," Eur. J. Pharm. Biopharm., 59:389-396 (2005).
Poduslo et al., "Polyamine modification increases the permeability of proteins at the blood-nerve and blood-brain barriers," J. Neurochem., 66:1599-1609 (1996).
Rajpal et al., A general method for greatly improving the affinity of antibodies by using combinatorial libraries, Proc. Natl. Acad. Sci. USA, 102:8466-71 (2005).
Reichert et al., "Monoclonal antibody successes in the clinic," Nat. Biotechnol., 23:1073-78 (2005).
Schaeffer et al., "The Rat Glomerular Filtration Barrier Does Not Show Negative Charge Selectivity," Microcirculation, 9:329-342 (2002).
Shaul, "Exploring the charge space of protein-protein association: a proteomic study," Proteins, 60:341-352 (2005).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Tarditi et al., "Selective high-performance liquid chromatographic purification of bispecific monoclonal antibodies," J. Chromatogr, 599:13-20 (1992).
Ten Kate et al., "Effect of isoelectric point on biodistribution and inflammation: imaging with indium-111-labelled IgG," Eur. J. Nucl. Med., 17:305-309 (1990).
Tsurushita et al., "Design of humanized antibodies: From anti-Tac to Zenapax," Methods, 36:69-83 (2005).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J. Pharmacol. Exp. Ther., 301:467-477 (2002).
Yang et al., "Tailoring structure-function and pharmacokinetic properties of single-chain Fv proteins by site-specific PEGylation," Protein Eng., 16:761-770 (2003).
Zuckier et al., "Chimeric human-mouse IgG antibodies with shuffled constant region exons demonstrate that multiple domains contribute to in vivo half-life," Cancer Res., 58:3905-08 (1998).
International Preliminary Report on Patentability for App. Ser. No. PCT/JP2007/057058, dated Oct. 21, 2008, 11 pages.
Japanese Patent Office, International Search Report App. Ser. No. PCT/JP2007/057058, mailed May 7, 2001, 2 pages.
European Search Report for App. Ser. No. 07 74 0494, dated Sep. 3, 2009, 3 pages.
USPTO Restriction Requirement in U.S. Appl. No. 12/295,075, dated Feb. 22, 2011, 9 pages.
USPTO Final Office Action in U.S. Appl. No. 10/575,905, mailed Feb. 24, 2011, 7 pages.
USPTO Notice of Allowance in U.S. Appl. No. 10/575,193, mailed Mar. 18, 2011, 12 pages.
USPTO Restriction Requirement in U.S. Appl. No. 11/910,836, dated Mar. 18, 2011, 7 pages.

Panka et al., "Variable region framework differences result in decreased or increased affinity of variant anti-digoxin antibodies," Proc. Natl. Acad. Sci. USA, 85(9):3080-84 (1988).
Chamow et al., "A humanized, bispecific immunoadhesin-antibody that retargets CD3+ effectors to kill HIV-1-infected cells," J. Immunol., 153(9):4268-80 (1994).
Fish & Richardson P.C., Amendment in U.S. Appl. No. 10/575,193, filed Jun. 17, 2011, 15 pages.
USPTO Notice of Allowance in U.S. App. No. 10/575,193, mailed Jul. 13, 2011, 8 pages.
Fish & Richardson P.C., Response to Restriction Requirement dated Feb. 22, 2011, in U.S. App. No. 12/295,075, filed Aug. 18, 2011, 2 pages.
Fish & Richardson P.C., Response to Restriction Requirement dated Mar. 18, 2011 in U.S. Appl. No. 11/910,836, filed Sep. 6, 2011, 1 page.
USPTO Non-Final Office Action in U.S. Appl. No. 11/910,836, dated Sep. 30, 2011, 21 pages.
Sinha et al., "Electrostatics in protein binding and function," Curr. Protein Pept. Sci., 3(6):601-14 (2002).
USPTO Non-Final Office Action in U.S. Appl. No. 12/295,075, dated Nov. 4, 2011, 14 pages.
Queen et al., "A humanized antibody that binds to the interleukin 2 receptor," *Proc. Natl. Acad. Sci. U.S.A.*, 86(24):10029-10033 (1989).
USPTO Final Office Action in U.S. Appl. No. 12/295,075, dated Jul. 19, 2012, 12 pages.
USPTO Restriction Requirement in U.S. Appl. No. 13/434,643, dated Jul. 27, 2012, 6 pages.
Gelderman et al., "The inhibitory effect of CD46, CD55, and CD59 on complement activation after immunotherapeutic treatment of cervical carcinoma cells with monoclonal antibodies or bispecific monoclonal antibodies," *Lab Invest.*, 82(4):483-93 (2002).
Kurfis et al., "Role of Arg182 in the second extracellular loop of angiotensin II receptor AT2 in ligand binding," *Biochem. Biophys. Res. Commun.*, 263:816-819 (1999).
Raffen et al., "Reengineering immunoglobulin domain interactions by introduction of charged residues," *Protein Eng.*, 11:303-309 (1998).
Fish & Richardson P.C., Response to Restriction Requirement dated Jun. 9, 2011 in U.S. Appl. No. 11/910,128, filed Dec. 2, 2011, 1 page.
USPTO Non-Final Office Action in U.S. Appl. No. 11/910,128, dated Apr. 25, 2012, 21 pages.
Fish & Richardson P.C., Amendment in Reply to Action dated Nov. 4, 2011 in U.S. Appl. No. 12/295,075, filed May 3, 2012, 12 pages.
Fish & Richardson P.C., Preliminary Amendment and Response to Restriction Requirement dated Jul. 27, 2012 in U.S. Appl. No. 13/434,643, filed Jan. 24, 2013, 10 pages.
Fish & Richardson P.C., Amendment in Reply to Action dated Jul. 19, 2012 in U.S. Appl. No. 12/295,075, filed Jan. 17, 2013, 113 pages.
Abe et al., "Purification of monoclonal antibodies with light-chain heterogeneity produced by mouse hybridomas raised with NS-1 myelomas: application of hydrophobic interaction high-performance liquid chromatography," *J. Biochem. Biophys. Methods*, 27:215-227 (1993).
Amersham Biosciences, "Protein Purification Handbook," Edition AC, 98 pages (2001).
Kranenborg et al., "Development and characterization of anti-renal cell carcinoma x antichelate bispecific monoclonal antibodies for two-phase targeting of renal cell carcinoma," *Cancer Res.*, 55:5864s-5867s (1995).
Lansdorp et al., "Purification and analysis of bispecific tetrameric antibody complexes," *Mol. Immunol.*, 27:659-666 (1990).
Morimoto et al., "Single-step purification of F(ab')2 fragments of mouse monoclonal antibodies (immunoglobulins G1) by hydrophobic interaction high performance liquid chromatography using TSKgel Phenyl-5PW," *J Biochem. Biophys. Methods*, 24:107-117 (1992).
Suresh et al., "Bispecific monoclonal antibodies from hybrid hybridomas," Methods Enzymol., 121:210-228 (1986).
Warnaar et al., "Purification of bispecific F(ab')2 from murine trinoma OC/TR with specificity for CD3 and ovarian cancer," *Hybridoma*, 13:519-526 (1994).

(56) References Cited

OTHER PUBLICATIONS

USPTO Restriction Requirement in U.S. Appl. No. 11/910,128, dated Jun. 9, 2011, 10 pages.

USPTO Non-Final Office Action in App. U.S. Appl. No. 13/434,643, dated Feb. 12, 2013, 17 pages.

Angal et al., "A single amino acid substitution abolishes the heterogeneity of chimeric mouse/human (IgG4) antibody," *Mol. Immunol.*, 30:105-108 (1993).

Atwell et al., "Stable heterodimers from remodeling the domain interface of a homodimer using a phage display library," *J. Mol. Biol.*, 270:26-35 (1997).

Fish & Richardson P.C., Amendment in Reply to Office Action dated Apr. 25, 2012 in U.S. Appl. No. 11/910,128, filed Oct. 25, 2012, 32 pages.

Fish & Richardson P.C., Supplemental Amendment in U.S. Appl. No. 11/910,128, filed Nov. 14, 2012, 20 pages.

International Preliminary Report on Patentability for App. No. PCT/JP2010/073361, dated Aug. 14, 2012, 7 pages.

Burges et al., "Effective relief of malignant ascites in patients with advanced ovarian cancer by a trifunctional anti-EpCAM × anti-CD3 antibody: a phase I/II study," *Clin. Cancer Res.*, 13(13):3899-905 (2007).

Kim et al., "Mapping the site on human IgG for binding of the MHC class I-related receptor, FcRn," *Eur. J. Immunol.*, 29(9):2819-25 (1999).

Morell et al., "Metabolic properties of IgG subclasses in man," *J. Clin. Invest.*, 49(4):673-80 (1970).

Ruf et al., "Pharmacokinetics and in vivo stability of intraperitoneally administered therapeutic antibody catumaxomab," *J. Clin. Oncol.*, 26 (May 20 suppl) (2008), abstr 14006.

Salfeld et al., "Isotype selection in antibody engineering," *Nat. Biotechnol.*, 25:1369-72 (2007).

Manz et al., Bioanalytical Chemistry, World Scientific Publishing Co., p. 7 (2003).

Smans et al., "Bispecific antibody-mediated lysis of primary cultures of ovarian carcinoma cells using multiple target antigens," *Int. J. Cancer*, 83:270-277 (1999).

U.S. Examiner Nelson B. Moseley II, USPTO Non-Final Office Action in U.S. Appl. No. 12/295,075, dated Jun. 7, 2013, 17 pages.

Fish & Richardson P.C., Amendment in Reply to Office Action dated Feb. 12, 2013 in U.S. Appl. No. 13/434,643, filed on May 13, 2013, 18 pages.

International Preliminary Report on Patentability for U.S. Appl. No. PCT/JP2011/076486, dated Jun. 12, 2013, 9 pages.

USPTO Final Office Action in U.S. Appl. No. 13/434,643, dated Jul. 11, 2013, 19 pages.

Aslan et al., "Engineering a novel, stable dimeric streptavidin with lower isoelectric point," *J. Biotechnol.*, 128(2):213-25 (2007).

Baerga-Ortiz et al., "Two different proteins that compete for binding to thrombin have opposite kinetic and thermodynamic profiles," *Protein Sci.*, 13(1):166-76 (2004).

Gunasekaran et al., "Enhancing antibody Fc heterodimer formation through electrostatic steering effects: applications to bispecific molecules and monovalent IgG," *J Biol. Chem.*, 285(25):19637-46 (2010).

Marti et al., "Inverse electrostatic effect: electrostatic repulsion in the unfolded state stabilizes a leucine zipper," *Biochemistry*, 43(39):12436-47 (2004).

Marvin et al., "Redesigning an antibody fragment for faster association with its antigen," Biochemistry, 42:7077-83 (2003).

USPTO Final Office Action in U.S. Appl. No. 11/910,128, dated Sep. 10, 2013, 12 pages.

\* cited by examiner

PROCESS FOR PRODUCING ANTIBODIES

CROSS-REFERENCE TO RELATED APPLICATIONS

This application is the National Stage of International Application No. PCT/JP2004/008585, filed Jun. 11, 2004, which claims the benefit of Japanese Patent Applications Serial No. 2003-167087, filed on Jun. 11, 2003, and International Application No. PCT/JP2003/14059, filed on Nov. 4, 2003. The contents of all of the foregoing applications are hereby incorporated by reference in their entireties.

TECHNICAL FIELD

The present invention relates to methods for preferentially producing desired antibodies when producing multispecific antibodies which bind multiple antibodies or antibody fragments. More specifically, the present invention relates to methods for producing antibodies in which contact is inhibited between the first light chain and the second heavy chain, which are not linked to the first heavy chain and second light chain respectively, and contact is inhibited between the first heavy chain and second light chain, which are not linked to the first light chain and second heavy chain respectively. In addition, the present invention relates to methods for increasing the specific activity of antibody compositions by using the above methods, and antibody compositions obtained by these methods, as well as vectors used in these methods, vector kits comprising the vectors, and cells comprising the vectors or vector kits.

BACKGROUND ART

An antibody is generally composed of two heavy (H) chains and two light (L) chains. A single H chain and single L chain are linked via a disulfide bond to form a H chain-L chain pair, and two such pairs are linked via two disulfide bonds between the H chains to form an antibody. Bispecific antibodies (BsAbs), also called bifunctional antibodies, are multivalent antibodies with specific binding sites for two antigenic determinants. They can react with two types of antigens. BsAbs can be produced using hybrid hybridomas, or more specifically quadromas, which are fusions of two different types of monoclonal antibody-producing cells (U.S. Pat. No. 4,474,893; R. Bos and W. Nieuwenhuitzen Hybridoma (1992) 11(1): 41-51). BsAbs can also be generated by linking Fab (antigen-binding) fragments or Fab' fragments of two types of monoclonal antibodies, using chemical techniques (M. Brennan et al. Science (1985) 229(1708): 81-3) or genetic engineering. In addition, BsAbs can be produced by covalently linking two complete monoclonal antibodies (B. Karpovsky et al. J. Exp. Med. (1984) 160(6): 1686-701).

Problems underlying BsAb production methods include the possibility of generating ten different types of antibody molecules due to the random combination of immunoglobulin H chains and L chains (M. R. Suresh et al. Methods Enzymol. (1986) 121: 210-28). Of these ten types of antibodies produced by quadromas, the only antibodies with the desired dual specificity are those with the correct L and H chain combination and which are composed of two L chain/H chain pairs with different binding specificities. Therefore, antibodies with the desired specificity must be selectively purified from the ten types of antibodies produced by quadromas. Purification is generally performed using affinity chromatography, but this method is laborious and low yielding (Y. S. Massimo et al. J. Immunol. Methods (1997) 201: 57-66).

Methods that overcome such problems and give higher BsAb yields include, for example, methods of chemically linking antibody fragments such as Fab'-thionitrobenzoic acid derivative and Fab'-thiol (SH) (Brennan et al. Science (1985) 229: 81). Furthermore, methods for more conveniently obtaining Fab'-SH fragments able to be chemically linked include methods for producing these fragments from hosts such as *E. coli* using genetic recombination techniques (Shalaby et al. J. Exp. Med. (1992) 175: 217-25). Genetic recombination techniques can also be used to obtain BsAbs composed of humanized antibody fragments. Diabodies (Db) are BsAbs constructed from the gene fusion of two types of fragments, and they comprise an L chain variable region (VL) connected to a H chain variable region (VH) by a linker that is too short to allow pairing between the two (P. Holliner et al. Proc. Natl. Acad. Sci. USA (1993) 90: 6444-8; EP No. 404, 097; WO93/11161). An example of such a Db that has been further improved is a single-chain Db (WO 03/087163). However, antibody fragments have a shorter serum half-life when compared to full-length antibodies, and do not have effector functions like complete antibodies do. Therefore, in some cases, full-length antibodies are more suitable for diagnosis and therapy.

Methods for efficiently linking generated antibody H chains into heterodimers include a method for introducing a sterically complementary mutation into the CH3 domain (a portion of the constant region) in the multimerized domain of an antibody H chain (Ridgway et al. Protein Eng. (1996) 9: 617-21). H chains produced by this method may still form pairs with the wrong L chains. Japanese Patent Kohyo Publication No. (JP-A (Kohyo)) 2001-523971 (unexamined Japanese national phase publication corresponding to a non-Japanese international publication) describes a method for generating multi-specific antibodies which share common light chains binding to heteromeric polypeptides with antibody-binding domains. However, when any two such antibodies are selected, they rarely share the same L chain, and the method is difficult to perform. Therefore, one of the present inventors proposed a method of screening for a common L chain that corresponds to an arbitrary different H chain and exhibits high affinity (PCT/JP04/000496).

BsAbs having specific binding capacities for two different antigens are useful as targeting agents in clinical fields such as in vitro and in vivo immunodiagnosis, therapy, and immunoassays. For example, they can be used as vehicles to link enzymes to carriers by designing a BsAb so that one of its arms binds to an epitope of an enzyme reaction non-inhibiting portion of an enzyme to be used in an enzyme immunoassay, and the other arm binds to a carrier for immobilization (Hammerling et al. J. Exp. Med. (1968) 128: 1461-73). Another example is antibody-targeted thrombolytic therapy. This therapy examines the use of antibodies that transport enzymes such as urokinase, streptokinase, tissue plasminogen activator, prourokinase, and their precursor proteins, in a manner specific to fibrin in thrombi (T. Kurokawa et al. Bio/Technology (1989) 7: 1163; Japanese Patent Application Kokai Publication No. (JP-A (Kokai)) H05-304992 (unexamined, published Japanese patent application)). Furthermore, there have also been reports of using BsAbs as mouse/human-chimeric bispecific antibodies applicable in cancer targeting (JP-A (Kokai) H02-145187), and in cancer therapy and diagnosis for various tumors (see for example, JP-A (Kokai) H05-213775; JP-A (Kokai) H10-165184; JP-A (Kokai) H11-71288; JP-A (Kohyo) 2002-518041; JP-A (Kohyo) H11-506310; Link et al. Blood (1993) 81: 3343; T. Nitta et al. Lancet (1990) 335: 368-71; L. deLeij et al. Foundation Nationale de Transfusion Sanguine, Les Ulis France (1990) 249-

53; Le Doussal et al. J. Nucl. Med. (1993) 34: 1662-71; Stickney et al. Cancer Res. (1991) 51: 6650-5), mycotic therapy (JP-A (Kokai) H05-199894), immune response induction (JP-A (Kohyo) H10-511085; Weiner et al. Cancer Res. (1993) 53: 94-100), induction of killer T-cell function (Kroesen et al. Br. J. Cancer (1994) 70: 652-61; Weiner et al. J. Immunol. (1994) 152: 2385), immunoanalysis (M. R. Suresh et al. Proc. Natl. Acad. Sci. USA (1986) 83: 7989-93; JP-A (Kokai) H05-184383), immunohistochemistry (C. Milstein and A. C. Cuello Nature (1983) 305:537), and such.

Specific antibodies for a certain antigen can be produced via genetic engineering, by obtaining the nucleotide sequences of the H and L chain variable regions which determine the antigen specificity of antibodies (J. Xiang et al. Mol. Immunol. (1990) 27: 809; C. R. Bebbington et al. Bio/Technology (1992) 10: 169). Methods for obtaining antigen-specific H and L chains include methods that utilize phages or phagemids using *E. coli* as the host (W. D. Huse et al. Science (1989) 246: 1275; J. McCafferty et al. Nature (1990) 348: 552; A. S. Kang et al. Proc. Natl. Acad. Sci. USA (1991) 88: 4363). In these methods, antibody libraries are constructed by generating Fabs, or by generating fusion proteins between a phage coat protein and Fab or a single-strand Fv. Finally, antigenic affinity is examined to select antigen-specific antibodies and their genes from these antibody libraries.

SUMMARY OF THE INVENTION

When expressing bispecific antibodies (BsAbs), most H chains are formed into heterologous combinations (Ha-Hb) using the knobs-into-holes technique; however, the L chains corresponding to the each H chain do not necessarily bind to the desired H chains. Thus, four possible combinations of H and L chains exist: HaLa-HbLb (the desired form), HaLb-HbLa, HaLa-HbLa, and HaLb-HbLb. Therefore, when producing a bispecific agonist IgG by simply expressing two H chains to which the knobs-into-holes technique is applied, and two L chains, the apparent specific activity of the IgG produced would be lower than expected because of the presence of undesired IgGs. Moreover, the desired IgG is not produced at a constant rate because the expression level of each chain can differ, or the affinity level of undesired H and L chain combinations can differ. In addition, there is no way of confirming the ratio of desired IgG versus total IgG produced. These problems make it difficult to screen for antibodies based on their agonist activity. The problems are likely to occur when producing multi-specific antibodies, including all BsAbs.

To solve the above problems, the present inventors paid attention to the fact that when using knobs-into-holes, antibodies with only a single H chain are not secreted, and they revealed that it is possible to preferentially form a desired BsAb as follows: H and L chains of one arm (Ha and La) are first expressed, their expressions are suppressed, and then the H and L chains of the other arm (Hb and Lb) are expressed so that the desired HL molecules (HaLa and HbLb) are first constructed and then the H chains are paired with each other ($H_2L_2$). Thus, the present inventors completed this invention. The present invention enables the efficient production of desired antibodies when producing multi-specific antibodies such as bispecific IgG, by inhibiting contact between H and L chains that do not correspond to each other. For example, this is achieved by respectively expressing the H and L chains on the left arm of an antibody (Left HL) and the H and L chains on the right arm of the antibody (Right HL) at different times using vectors that allow regulated expression.

More specifically, the present invention provides:

[1] a method for producing an antibody wherein the method comprises inhibiting contact between a first light chain (L chain) and a second heavy chain (H chain), which are not linked to a first H chain and a second L chain respectively, and inhibiting contact between a first H chain and a second L chain, which are not linked to a first L chain and a second H chain respectively;

[2] a method for producing an antibody wherein the method comprises expressing a first pair and a second pair of the antibody at different times;

[3] a method for producing an antibody, wherein the method comprises the following steps, (a) expressing a first H chain and a first L chain to prepare a first pair of the antibody, (b) expressing a second H chain and a second L chain to prepare a second pair of the antibody, and (c) preparing the antibody using the first pair and the second pair;

[4] a method for producing an antibody wherein the method comprises the following steps, (a) inducing the expression of a first H chain and a first L chain to prepare a first pair of the antibody, (b) turning off the induced expression of the first H chain and the first L chain, (c) inducing the expression of a second H chain and a second L chain to prepare a second pair of the antibody, and (d) preparing the antibody using the first pair and the second pair;

[5] the method of any one of [1] to [4,] wherein the amino acid sequences of the first and the second H chains are different, and the amino acid sequences of the first and the second L chains are different;

[6] the method of any one of [1] to [5], wherein the antibody is a bispecific antibody;

[7] the method of any one of [1] to [6], wherein the antibody is unlikely to be formed from a combination of just the first pairs or the second pairs;

[8] the method of any one of [1] to [7], wherein the antibody which is unlikely to be formed from a combination of just the first pairs or the second pairs is prepared using the knobs-into-holes technique;

[9] a method for producing an antibody, the method comprising using a vector in which expressions of a first H chain and a first L chain can be induced by a first expression regulator; and a vector in which expressions of a second H chain and a second L chain can be induced by a second expression regulator;

[10] a method for increasing the specific activity of an antibody composition by increasing the proportion of an antibody that comprises a first pair and a second pair in the antibody composition;

[11] a method for increasing the specific activity of an antibody composition by expressing a first pair and a second pair of the antibody at different times;

[12] a method for suppressing the production of antibodies other than an antibody comprising a first pair and a second pair by expressing the first pair and the second pair of the antibody at different times;

[13] a method for expressing a first pair and a second pair of an antibody at different times, wherein the method comprises using two or more distinct expression inducing agents;

[14] an antibody produced according to any one of [1] to [9];

[15] an antibody composition having a high proportion of an antibody comprising a first pair and a second pair, compared to an antibody composition produced by simultaneously expressing a first and a second H chains, and a first and a second L chains;

[16] the antibody composition of [15], wherein the L and H chains of the antibody are not linked by a peptide linker;

[17] a vector in which expression of an L chain or an H chain of an antibody can be induced by an expression inducing agent;

[18] a vector kit comprising a vector in which expression of a first L chain and a first H chain of an antibody can be induced by a first expression regulator; and a vector in which expression of a second L chain and a second H chain of the antibody can be induced by a second expression regulator;

[19] a cell comprising a vector of [17] or [18]; and

[20] a cell capable of expressing a first pair and a second pair of an antibody at different times.

1. Methods for Producing Antibodies

Figure 1:
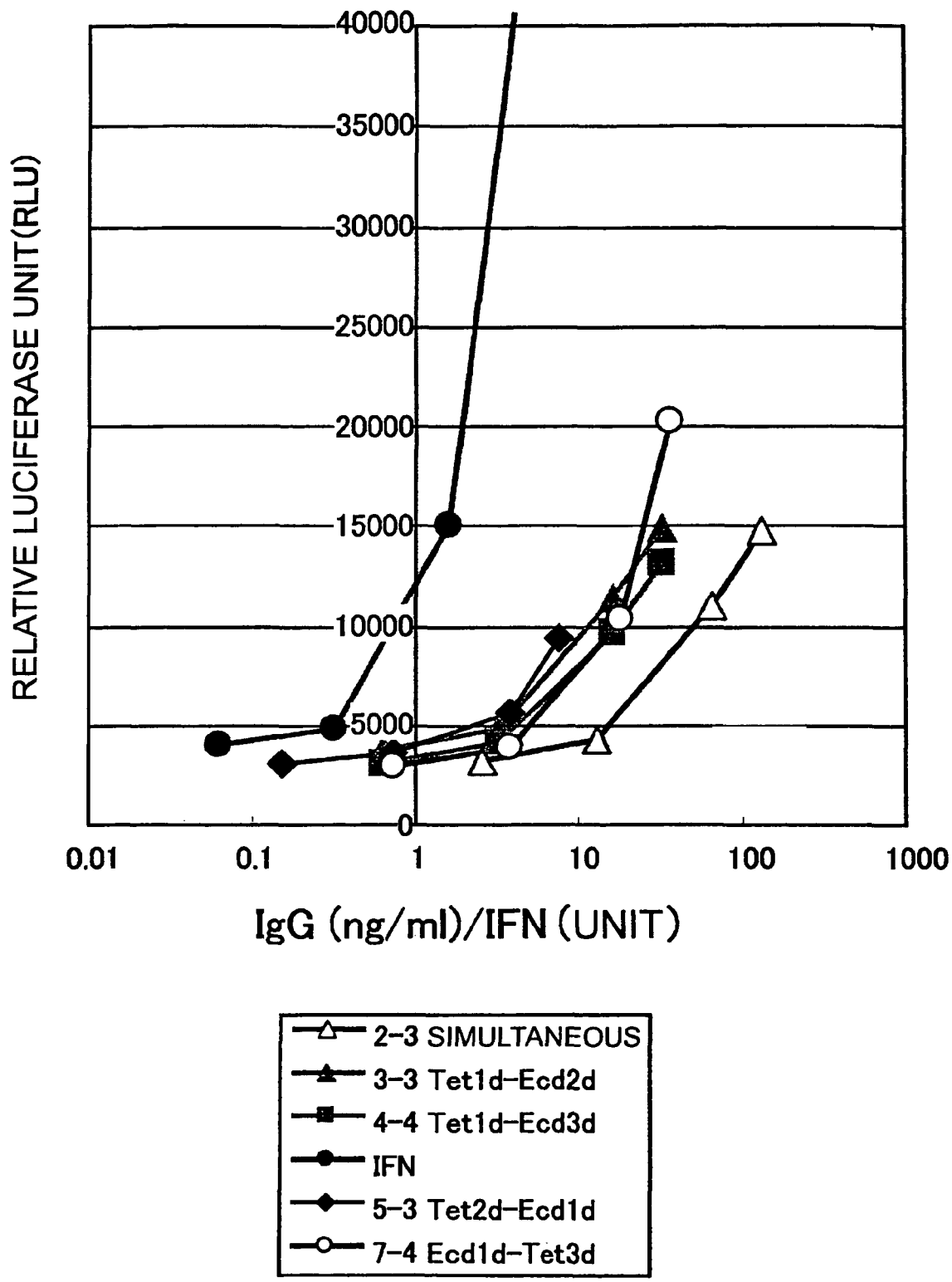
FIG. 1 shows a graph comparing IFN agonist activities using a quantitative luciferase assay. 2-3: Simultaneous induction; 3-3: tetracycline induction for one day followed by muristerone A induction for two days; 4-4: tetracycline induction for one day followed by muristerone A induction for three days; 5-3: tetracycline induction for two days followed by muristerone A induction for one day; 7-4: muristerone A induction for one day followed by tetracycline induction for three days.
Figure 2:
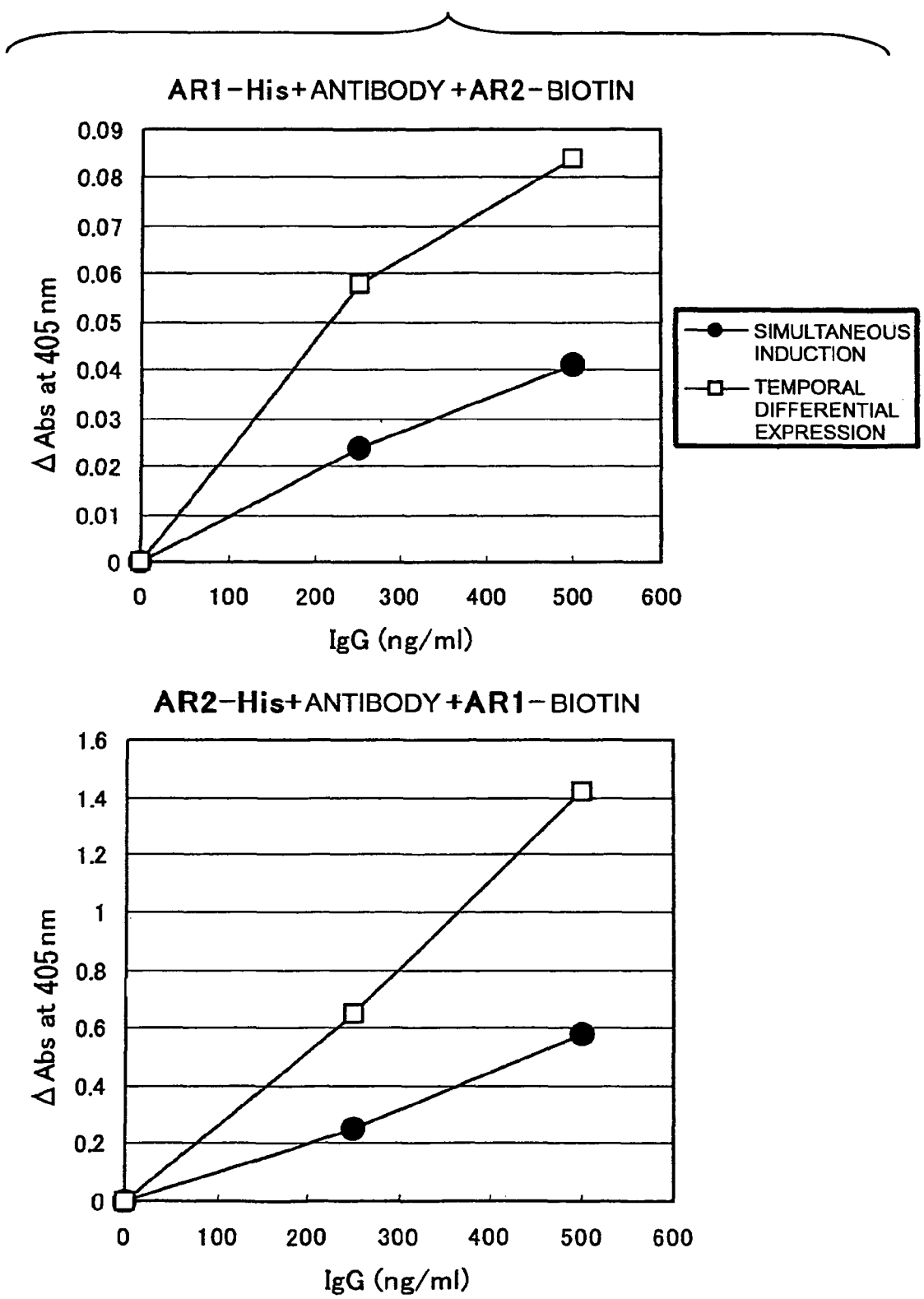
FIG. 2 shows graphs comparing the amounts of antibodies of a desired type by sandwich ELISA. Absorbance at 405 nm with a reference wavelength at 655 nm was measured for each antibody sample at the indicated concentrations. The top graph shows the results for AR1-His+Antibody+AR2-biotin, and the bottom graph shows the results for AR2-His+Antibody+AR1-biotin. Filled circles: samples expressed by simultaneous induction; open squares: samples expressed by induction at different times.

The present invention relates to methods for preferentially producing desired antibodies when producing multi-specific antibodies which bind to multiple antibodies or antibody fragments. More specifically, in the process of producing multi-specific antibodies such as bispecific antibodies (BsAbs), a desired BsAb form can be produced by inhibiting contact between the first L chain and the second H chain, which are not linked to the first H chain and the second L chain respectively, and inhibiting contact between the first H chain and the second L chain, which are not linked to the first L chain and the second H chain respectively. In the present invention, a desired BsAb can be preferentially produced by (1) expressing the first H and L chains of an antibody to prepare the first H-L chain pair, (2) separately expressing the second H and L chains of the antibody to prepare the second H-L chain pair, and then (3) producing a desired BsAb using the two pairs produced in steps (1) and (2). In addition, when aiming to produce antibodies with three or more specificities, a desired number of H and L chain pairs are separately expressed to form each of the pairs, and then the formed pairs are used to produce the desired multi-specific antibody, as described for the production of BsAbs. Explanations hereinafter use BsAb as an example of a multi-specific antibody, but the methods of the present invention can be applied to other multi-specific antibodies in the same way.

Herein, if a desired multi-specific antibody is a BsAb, "the first heavy (H) chain" means one of the two H chains composing the antibody, and "the second H chain" means the other H chain, which is different from the first H chain. Thus, any one of the two H chains may be defined as the first H chain and the other may be defined as the second H chain. In the same way, "the first light (L) chain" means one of the two L chains composing the BsAb, and "the second L chain" means the other L chain, which is different from the first L chain. Any one of the two L chains may be defined as the first L chain and the other may be defined as the second L chain. Normally, the first L and H chains are derived from the same antibody, which recognizes a given antigen (or epitope), and the second L and H chains are derived from the same antibody, which recognizes another antigen (or epitope), but they are not limited thereto. Herein, the pair formed by the first H and L chains is called the first pair, and the pair formed by the second H and L chain is called the second pair. An antigen (or epitope) used for preparing the antibody from which the second pair is derived is preferably different from that used for preparing the antibody from which the first pair is derived. That is, the first and second pairs may recognize the same antigen, but preferably recognize different antigens (or epitopes). In this case, the H chains and L chains in the first and second pairs preferably comprise amino acid sequences that are different from each other. If the first and second pairs recognize different antigen determinants, the first and second pairs may recognize completely different antigens, or different sites (different epitopes) on the same antigen. In addition, one pair may recognize an antigen such as a protein, peptide, gene, and sugar, and the other may recognize a radioactive substance, chemotherapeutic agent, or cytotoxic substance such as a cell-derived toxin. However, when producing an antibody containing particular H and L chain pairs, the H and L chains may be arbitrarily selected as the first or second pair.

Known sequences can be used as the genes encoding the H chains or L chains of antibodies, or such genes can be obtained by methods known in the art. For example, the genes may be obtained from antibody libraries, or by cloning antibody-encoding genes from hybridomas that produce monoclonal antibodies.

Those skilled in the art can appropriately obtain antibody libraries since many antibody libraries are already known and methods for producing antibody libraries are commonly known. For example, antibody phage libraries may be obtained according to the methods described in the following literature: Clackson et al. Nature 352: 624-628 (1991); Marks et al. J. Mol. Biol. 222: 581-597 (1991); Waterhouses et al. Nucleic Acid Res. 21: 2265-2266 (1993); Griffiths et al. EMBO J. 13: 3245-3260 (1994); Vaughan et al. Nature Biotechnology 14: 309-314 (1996); JP-A (Kohyo) H10-504970. Alternative known methods can also be used, such as methods using eukaryotic cells as a library (WO95/15393 pamphlet), or ribosome display methods. Further, techniques for obtaining human antibodies by panning using a human antibody library are also known. For example, variable regions of human antibodies can be expressed as single chain antibodies (scFvs) on the surface of phages using phage display methods, and those phages which bind antigens can be selected. The genes of selected phages can be analyzed to determine the nucleotide sequence encoding the variable regions of the human antibody that bind an antigen. Once the nucleotide sequence of the scFv that binds to the antigen has been determined, a human antibody can be obtained by preparing a suitable expression vector based on that sequence. Such methods are already well known (see WO92/01047, WO92/20791, WO93/06213, WO93/11236, WO93/19172, WO95/01438, and WO95/15388).

Antibody-encoding genes may be obtained from hybridomas using known techniques. A desired antigen or cells expressing such are used as sensitizing antigens, and immunization is performed according to standard methods. The obtained immune cells are fused with known parental cells using standard cell fusion methods, and monoclonal antibody-producing cells (hybridomas) are screened using standard screening methods. mRNAs are isolated from the obtained hybridomas. cDNAs encoding the antibody variable regions (V regions) are synthesized from the mRNAs using a reverse transcriptase, and these are then ligated to a DNA encoding a desired antibody constant region (C region).

More specifically, sensitizing antigens for obtaining genes encoding the antibody H and L chains of the present invention comprise both complete antigens with immunogenicity, and incomplete antigens without immunogenicity, such as hapten, but are not limited thereto. For example, an entire desired protein or its partial peptide may be used. In addition, substances composed of polysaccharides, nucleic acids, lipids, or such can be used as antigens. Therefore the antigens for the antibodies of the present invention are not particularly limited. Antigens may be prepared using methods known in the art, for example, methods using Baculovirus (for example, WO98/46777). Hybridomas may be prepared, for example, by the method of Milstein et al. (Kohler G and Milstein C. Methods Enzymol. 73: 3-46 (1981)). If the immunogenicity of an antigen is poor, the antigen may be conjugated with a macromolecule with immunogenicity, such as albumin, for immunization. In addition, if necessary, an antigen may be conjugated with other molecules to prepare a soluble antigen. If a transmembrane molecule such as a receptor is used as an antigen, a fragment of the extracellular domain of the receptor may be used, and a cell expressing the transmembrane molecule on the cell surface may also be used as an antigen.

Antibody-producing cells can be obtained by immunizing animals using appropriate sensitizing antigens. Alternatively, antibody-producing cells can be prepared by in vitro immunization of lymphocytes that can produce antibodies. Various mammals can be used as immunizing animals, and primates and Rodentia and Lagomorpha animals are generally used. Examples of such animals include mice, rats, and hamsters for Rodentia, rabbits for Lagomorpha, and monkeys including cynomolgus monkeys, rhesus monkeys, hamadryas, and chimpanzees for primates. In addition, transgenic animals carrying human antibody gene repertoires are known, and human antibodies can be obtained by using such animals (see, WO96/34096; Mendez et al. (1997) Nat. Genet. 15: 146-56).

Instead of using such transgenic animals, for example, human lymphocytes may be immunized with a desired antigen or cells expressing the same in vitro, and the immunized lymphocytes may be fused with human myeloma cells such as U266 cells to obtain a desired human antibody with binding activity to the antigen (Japanese Patent Application Kokoku Publication No. (JP-B) H01-59878 (examined, approved Japanese patent application published for opposition)). Alternatively, a transgenic animal expressing the entire repertoire of human antibody genes may be immunized with a desired antigen to obtain a desired human antibody (see WO93/12227, WO92/03918, WO94/02602, WO96/34096, and WO96/33735).

Animal immunization can be carried out, for example, by appropriately diluting and suspending a sensitizing antigen in Phosphate-Buffered Saline (PBS), physiological saline, or such, and forming an emulsion by mixing an adjuvant as necessary, followed by intraperitoneal or subcutaneous injection into animals. After that, the sensitizing antigen mixed with Freund's incomplete adjuvant is preferably administered several times every four to 21 days. Antibody production can be confirmed by using conventional methods to measure the target antibody titer in animal sera.

Antibody-producing cells obtained from lymphocytes or animals immunized with a desired antigen can be fused with myeloma cells to generate hybridomas by using conventional fusing agents such as polyethylene glycol (Goding, Monoclonal Antibodies: Principles and Practice, Academic Press, 1986, 59-103). Hybridoma cells are cultured and grown as required, and the binding specificity of the antibodies produced from these hybridomas is analyzed using known methods such as immunoprecipitation, radioimmunoassay (RIA), and enzyme-linked immunosorbent assay (ELISA). Thereafter, hybridomas producing antibodies found to have the desired specificity, affinity, or activity can be subcloned as required using methods such as limiting dilution.

Next, genes encoding the selected antibodies can be cloned from hybridomas or antibody-producing cells (sensitized lymphocytes, and such) using probes that can bind specifically to the antibodies (for example, oligonucleotides that are complementary to sequences encoding the antibody constant regions). Cloning from mRNA using RT-PCR is also possible. Immunoglobulins are classified into five different classes, IgA, IgD, IgE, IgG, and IgM, which are further divided into several subclasses (isotypes) (for example, IgG-1, IgG-2, IgG-3, and IgG-4; IgA-1 and IgA-2; and such). The H and L chains used to produce antibodies in the present invention may be derived from any antibody belonging to any one of the above classes and subclasses. They are not particularly limited, but IgG is particularly preferable.

Herein, genes encoding the H and L chains may be modified by gene engineering techniques. For example, antibodies from animals such as mice, rats, rabbits, hamsters, sheep, and camels may be appropriately made into genetically recombinant antibodies such as chimeric antibodies and humanized antibodies, which are artificially modified so as to reduce heterologous antigenicity in humans. A chimeric antibody consists of the constant H and L chain regions from a human antibody and the variable H and L chain regions of an antibody from a non-human mammal, such as mouse. Such chimeric antibodies may be obtained by ligating a DNA that encodes the variable region of a mouse antibody with a DNA that encodes the constant region of a human antibody, integrating the DNA into an expression vector, and introducing the vector into a host to produce the antibody. A humanized antibody is also called a reshaped human antibody, and can be prepared as follows: A DNA sequence designed to link to the complementary determining region (CDR) of an antibody from a non-human mammal, such as mouse, is synthesized by PCR using several oligonucleotides prepared so as to have overlapping ends. The obtained DNA is ligated with a DNA encoding the constant region of a human antibody, integrated into an expression vector, and then introduced into a host to produce a humanized antibody (EP239400; WO96/02576). The framework region (FR) of the human antibody linked via the CDR may be selected so that it forms a suitable antigen binding site. If necessary, the amino acid sequence of the FR in the variable region of the reshaped human antibody may be substituted so that the CDR can form an appropriate antigen binding site (Sato K. et al. Cancer Res. 53: 851-856 (1993)).

In addition to the humanization described above, antibodies may be modified to improve their biological characteristics, for example, their antigen binding capacity. Such modifications can be made using methods such as site-directed mutagenesis (see for example, Kunkel Proc. Natl. Acad. Sci. USA (1985) 82: 488), PCR mutagenesis, and cassette mutagenesis. In general, mutant antibodies whose biological characteristics have been improved show amino acid sequence homology and/or similarity of 70% or higher, more preferably 80% or higher, and even more preferably 90% or higher (for example, 95% or higher, 97%, 98%, or 99%) to the original antibody variable region. Herein, sequence homology and/or similarity is defined as the ratio of amino acid residues that are homologous (the same residue) or similar (amino acid residues classified into the same group based on the general characteristics of amino acid side chains) to the original antibody residues, after maximizing the sequence homology value by aligning sequences and introducing gaps as necessary. Generally, naturally-occurring amino acid residues are classified into groups based on the characteristics of their side chains: (1) hydrophobic: alanine, isoleucine, norleucine, valine, methionine, and leucine; (2) neutral hydrophilic: asparagine, glutamine, cysteine, threonine, and serine; (3) acidic: aspartic acid, and glutamic acid; (4) basic: arginine, histidine, and lysine; (5) residues that affect the orientation of the chains: glycine, and proline; and (6) aromatic: tyrosine, tryptophan, and phenylalanine.

Normally, the antigen binding site of an antibody is formed by interactions among the total of six complementary determining regions (hypervariable region CDRs) in the variable regions of the H and L chains. Although its affinity is lower than that of the entire antigen binding site, even one of these variable regions can recognize and bind an antigen. Thus, the genes encoding H and L chains of the antibodies of the present invention may be any form, as long as the polypeptides encoded by the genes retain the ability to bind to a desired antigen, and encode partial fragments comprising the each of the antigen binding sites of the H and L chains.

Furthermore, the genes encoding H chains of the present invention are preferably designed so that the antibodies expressed from the genes are unlikely to be formed from a combination of just the first pairs or just the second pairs. For example, the knobs-into-holes technique (JP-A (Kohyo) 2001-523971), a method known to those skilled in the art, introduces a specific and complementary interaction at the interfaces of the first and second polypeptides (for example, introducing a residue containing a free thiol to the interface of the first polypeptide and a corresponding residue containing a free thiol to the interface of the second polypeptide, so that a non-natural disulfide bond can be formed between the first and second polypeptides). This method enables the expression of H chains while promoting the formation of heteromultimers and suppressing the formation of homomultimers.

In order to inhibit contact between the first L chain and second H chain, which are not linked to the first H chain and second L chain respectively, and contact between the first H chain and second L chain, which are not linked to the first L chain and second H chain respectively, the first H chain and second L chain may be expressed at different times, and the first L chain and second H chain may be expressed at different times. For example, methods for expressing the first and second pairs at different times may be employed.

In contrast to expressing the first and second pairs at different times as above, if the pairs are expressed simultaneously, neither the contact between the first L chain and second H chain, which are not linked to the first H chain and second L chain respectively, nor the contact between the first H chain and second L chain, which are not linked to the first L chain and second H chain respectively, are normally inhibited. Therefore, neither the binding between the first L chain and second H chain that are not linked with the first H chain and second L chain respectively, nor the binding between the first H chain and second L chain that are not linked with the first L chain and second H chain respectively, are suppressed.

Herein, "expressing the first and the second pairs simultaneously" means that the time in which the first pair is expressed overlaps at least partially with that in which the second pair is expressed, and preferably it means that the times when the first and second pairs are expressed match exactly.

In the present invention, if the first and second pairs are expressed at different times, it is preferable that the time at which the first pair is expressed and the time at which the second pair is expressed are completely different; that is, when the first pair is expressed, the second pair is not expressed, and when the second pair is expressed, the first pair is not expressed. However, the present invention is not limited thereto, and the time in which the first pair is expressed may overlap partially with that in which the second pair is expressed. In an alternative method for suppressing the binding between the first H chain and second L chain, and the binding between the second H chain and first L chain, the first H chain and second L chain may be expressed at different times, and the second H chain and first L chain may be expressed at different times. Thus, in the methods of the present invention, it is preferable to express the first H chain and first L chain simultaneously, but the methods are not limited thereto, and the first H chain and first L chain may be expressed at different times (this is also the case for the second H chain and second L chain). In such cases, for example, inhibition of the contact between the first L chain and second H chain that are not linked to the first H chain and second L chain respectively, and contact between the first H chain and second L chain that are not linked to the first L chain and second H chain respectively, allows inhibition of the binding between the first H chain and second L chain and the binding between the first L chain and second H chain. For example, the first and second pairs can be expressed at different places so as to form the respective pairs separately, and they can then be contacted with each other to prepare an antibody. An example of such methods is where the first pair and second pair are expressed in different cells, allowed to form their respective pairs, and then the cells expressing these first and second pairs are fused to prepare an antibody.

Specific examples of methods for expressing the first and second pairs at different times include methods that induce the expression of the first and second pairs at different times using expression regulators and such. More specifically, a vector in which expression of a first pair can be induced by a first expression regulator, and a vector in which expression of a second pair is inducible by a second expression regulator, are constructed. The first pair and second pair may be constructed in a single vector, or two or more different vectors. Alternatively, the H chain and L chain may be constructed in a single vector, or two or more different vectors. Next, the obtained vector constructs are introduced into cells, and expression of the first pair is induced by the first expression regulator, and then expression of the second pair is induced by the second expression regulator. In this case, expression of the first pair is preferably turned off before expression of the second pair is induced.

The expression regulators are not particularly limited, and any kinds of expression regulators may be used as long as they can regulate expression of H chains and L chains in host cells. For example, expression may be induced in the presence of an expression regulator, and not in its absence; or conversely, expression may be induced in the presence of an expression regulator, and not in its absence. Expression regulators may be chemical compounds such as expression inducing agents, or physical factors such as temperature (heat). Specific examples of expression inducing agents include antibiotics such as tetracycline, hormones such as ecdysone analogues, and enzymes such as Cre (a homologous recombination enzyme which causes recombination). In addition, induced expression of an H chain and/or L chain may be halted by removing the expression inducing agent that functions as an above-mentioned expression regulator. If a physical factor such as temperature (heat) is used as an expression regulator, the induced expression of an H chain and/or L chain can be halted by returning to a temperature that does not permit induction of expression.

A vector whose expression can be induced by an expression regulator may be constructed using methods known to those skilled in the art. For specific example, such a vector can be constructed by introducing a gene which encodes the first or second pair of an antibody into a commercially available vector whose expression can be induced by an expression inducing agent (for example, pcDNA4/TO, pIND (Invitrogen)). Normally, the first expression regulator, which is used to induce expression of the H and L chains of the first pair, is different from the second expression regulator, which is used to induce expression of the H and L chains of the second pair. In some cases, the expression regulator for inducing the H chain of the first pair may be different from that for inducing the L chain of the first pair (this is also the case for expression regulators for the H and L chains of the second pair). Vectors constructed as above in which the expression of the first or second pair of an antibody is induced by an expression regulator, can express the first and second pairs of an antibody at different times. In addition, host cells transfected with such vectors can express the first and second pairs of the antibody at different times.

To construct vectors to express the respective antibody fragments of the present invention, regulatory units for transcription/translation of genetic information, such as promoters and terminators, are required, and an appropriate signal sequence is preferably placed at the N-terminus of the respective antibody fragments. Promoters such as those derived from lac, trp, tac, λ phage PL, and PR may be used. Terminators such as those derived from trpA, phages, and rrnB ribosomal RNA may be used. Appropriate signal sequences include a leader peptide sequence that allows secretion of a fusion protein from host cells, such as pel1B (Better et al. Science 240: 1041-1043 (1988); Sastry et al. Proc. Natl. Acad. Sci. U.S.A. 86: 5728 (1989)).

The vectors used to construct vectors that can express the first and second pairs of an antibody of the present invention at different times are not particularly limited, and any vector may be used. Specific examples of the vectors include expression vectors derived from mammals (for example, pcDNA3 (Invitrogen), pEF-BOS (Nucleic Acid Res. 18(17): 5322 (1990)), pEF, and pCDM8), expression vectors derived from insect cells (for example, the "Bac-to-Bac Baculovirus expression system" (Gibco BRL), pBacPAK8), expression vectors derived from plants (for example, pMH1 and pMH2), expression vectors derived from animal viruses (for example, pHSV, pMV, and pAdexLcw), expression vectors derived from retroviruses (for example, pZIPneo), yeast-derived expression vectors (for example, the "*Pichia* Expression Kit" (Invitrogen), pNV11, SP-QO1), expression vectors derived from *Bacillus subtilis* (for example, pPL608 and pKTH50), and expression vectors derived from *E. coli* (M13 series vectors, pUC series vectors, pBR322, pBluescript, and pCR-Script). Commercially available vectors in which expression can be induced by an expression inducing agent may also be used.

The cells used to prepare the cells that allow expression of the first and second pairs of an antibody of the present invention at different times are not particularly limited, and any cells may be used. If eukaryotic cells are used as a host, animal cells, plant cells, or fungi cells can be used. Animal cells known for such use include: (1) mammalian cells such as CHO, COS, myeloma, baby hamster kidney (BHK), HeLa, and Vero cells, (2) amphibian cells such as *Xenopus laevis* oocytes, or (3) insect cells such as Sf9, Sf21, and Tn5 cells. Plant cells such as those derived from the genus *Nicotiana*, for example, from *Nicotiana tabacum* are known, and may be cultured as calluses. As fungus cells, yeasts (cells derived from the genus *Saccharomyces*, such as *Saccharomyces cerevisiae*), filamentous fungi (cells from the genus *Aspergillus*, such as *Aspergillus niger*) and such are known. If prokaryotic cells are used, production systems using bacterial cells are available. As the bacterial cells, *E. coli* and *Bacillus subtilis* and such are known. In the present invention, the use of animal cells is preferable in view of glycosylation, tertiary structure conservation and so on, and the use of mammalian cells is particularly preferable. The cells of the present invention can be prepared by introducing a vector that can express the first and second pairs (in some cases, the respective H and L chains of the first and second pairs) of an antibody of the present invention at different times.

Methods for introducing the vector constructs that express the respective pairs into desired host cells depend on the type of the vectors and host cells. If a prokaryotic cell is used as a host cell, the vector may be introduced into the host cell by methods such as those using calcium ions (Proc. Natl. Acad. Sci. U.S.A. 69: 2110 (1972)), protoplast (JP-A (Kokai) S63-24829) and electroporation (Gene 17: 107 (1982); Molecular & General Genetics 168: 111 (1979)). If the host cell is a yeast, methods using electroporation (Methods Enzymol. 194: 182 (1990)), spheroplasts (Proc. Natl. Acad. Sci. U.S.A. 81: 4889 (1984)), lithium acetate (J. Bacteriol. 153: 163 (1983)), and such may be used. If the host is a plant cell, methods such as those using Agrobacterium (Gene 23: 315 (1983); WO89/05859, and so on) and sonication (WO91/00358) are known. When a mammalian cell is used as a host, methods for introducing the vector include those using electroporation (Cytotechnology 3: 133 (1990)), calcium phosphate (JP-A (Kokai) H2-227075), lipofection (Proc. Natl. Acad. Sci. USA 84: 7413 (1987); Virology 52: 456 (1973)), calcium phosphate coprecipitation, DEAE-dextran, and direct injection of DNA with microcapillaries.

The host cells thus obtained can be cultured, for example, by the following methods: When the host cells are prokaryotes or eukaryotic microorganisms, the culture media can be natural or synthetic, as long as they comprise essential substances for growth, such as carbon and nitrogen sources and inorganic salts which can be assimilated by the organisms, and allow efficient culture of the transformants. Culture may be carried out under aerobic or anaerobic conditions, and other conditions such as temperature, pH of the media, and duration of the culture can be appropriately determined by those skilled in the art, depending on the type of transformant. When using expression vectors equipped with inducible promoters, inducers may be added to the media as necessary (for example, IPTG for the lac promoter, and IAA for the trp promoter). When using insect cells as a host, media such as TNM-FH medium (Pharmingen), Sf-900 II SFM (Life Technologies), ExCell400 and ExCell405 (JRH Biosciences), and Grace's Insect Medium (Nature 195: 788 (1962)) may be used. If necessary, antibiotics such as gentamicin may be added to the media. If animal cells are used as host cells, common media such as RPMI1640 (The Journal of American Medical Association 199: 519 (1967)), Eagle's MEM (Science 122: 501 (1952)), DMEM (Virology 8: 396 (1959)), 199 medium (Proceeding of the Society for the Biological Medicine 73: 1 (1950)), and those supplemented with BSA and so on can be used. Culture can be carried out under normal conditions, such as pH 6 to 8, 30° C. to 40° C., and 5% $CO_2$. If necessary, antibiotics such as kanamycin and penicillin may be added to the media.

Methods for cloning an antibody-encoding gene into a suitable vector, introducing this into a host, and producing the antibody using recombinant DNA techniques are well known to those skilled in the art (for example, Carl, A. K. Borrebaeck & James, W. Larrick THERAPEUTIC MONOCLONAL ANTIBODIES, Published in the United Kingdom by MACMILLAN PUBLISHERS LTD. (1990)).

A specific example of the methods for producing antibodies of the present invention is given below. First, the H and L chains on the left arm of an antibody (Left HL) and the H and L chains on the right arm of the antibody (Right HL) are respectively cloned into a tetracycline inducible pcDNA4 vector (Invitrogen) and an ecdysone inducible pIND vector (Invitrogen). All of the expression-regulated plasmids are introduced into the above-mentioned suitable host cells, for example, animal cells such as COS-7 cells. For example, for the first induction tetracycline is added to the medium, and a Left HL molecule is formed in the cells. One to two days after the first induction, the medium is washed away to completely remove the first agent (tetracycline, in this case). Next, the cells are placed in a fresh medium containing an ecdysone analogue, the agent for the second induction, and the second induction is conducted for two to three days. Consequently, a Right HL molecule is produced and associates with the Left HL molecule already present in the cells, thus forming a complete BsAb form, which is then secreted into the medium.

The methods for producing antibodies of the present invention enable suppression of the production of antibodies other than those containing both the first and second pairs, and enable an increase in the proportion of antibodies containing both the first and second pairs in the antibody compositions produced. Thus, the methods of the present invention make it possible to increase the specific activity of the produced antibody compositions.

2. Antibodies

The present invention provides the antibodies produced by the methods described above. The antibodies in the antibody compositions produced by the above methods may be purified using known standard methods for protein purification, as necessary. For example, affinity columns such as Protein A columns, chromatography columns, filtration, ultrafiltration, salting out, and dialysis may be selected and appropriately combined to separate and purify antibodies (Antibodies: A Laboratory Manual. Ed Harlow and David Lane Cold Spring Harbor Laboratory (1988)). Purification may be performed, for example, using the antigen binding activity of an antibody as a marker. Antigen binding activity can be measured by known methods (Antibodies: A Laboratory Manual. Ed Harlow and David Lane Cold Spring Harbor Laboratory (1988)). For example, enzyme-linked immunosorbent assays (ELISA), enzyme immunoassays (EIA), radio immunoassays (RIA), immunofluorescence, or such may be used.

The multi-specific antibodies produced in the present invention are not particularly limited, but are normally bispecific antibodies (BsAbs) in which the first H chain and second H chain have a different amino acid sequence, and the first L chain and second L chain have a different amino acid sequence. Hereinafter the descriptions are mostly of BsAb, but these descriptions can be applied to other multi-specific antibodies. The first pair and second pair of a BsAb may recognize the same antigen, but preferably recognize different antigens (or epitopes). Herein, a BsAb may recognize completely different antigens or different sites (epitopes) on the same antigen. In addition, one pair may recognize an antigen such as a protein, peptide, gene, or sugar, and the other pair may recognize a radioactive substance, chemotherapeutic agent, or cytotoxic substance such as a cell-derived toxin, etc.

An antibody produced in the present invention is preferably designed so that the antibody is unlikely to be formed by association between the first pairs or between the second pairs. For example, knobs-into-holes engineering may be used. Knobs-into-holes engineering introduces a specific and complementary interaction on the interface between the first and second polypeptides to promote hetero-multimer formation and suppress homo-multimer formation (for example, a residue containing a free thiol and a corresponding residue containing a free thiol are introduced onto the interface between the first and second polypeptides respectively, thus forming a non-natural disulfide bond between the first and second polypeptides) (JP-A (Kohyo) 2001-523971). The knobs-into-holes technique is known to those skilled in the art, and they can suitably apply it to antibodies.

In addition, the antibodies produced in the present invention are preferably antibodies in which the H and L chains are not linked with a linker or such, or more preferably antibodies in which there is no covalent bond except disulfide bonds present between the H and L chains.

Moreover, the antibodies can be minibodies such as antibody fragments, or modified antibodies, as long as they bind to an antigen. Examples of such antibody fragments are Fab, Fab', F(ab')2, Fv, diabodies, etc. Such antibody fragments can be obtained by constructing a gene encoding an antibody fragment, introducing it into an expression vector, and expressing the vector in a suitable host cell (for example, Co M. S. et al. J. Immunol. 152: 2968-2976 (1994); Better M. and Horwitz A. H. Methods Enzymol. 178: 476-496 (1989); Pluckthun A. and Skerra A. Methods Enzymol. 178: 497-515 (1989); Lamoyi E. Methods Enzymol. 121: 652-663 (1986); Rousseaux J. et al. Methods Enzymol. 121: 663-669 (1986); Bird R. E. and Walker B. W. Trends Biotechnol. 9: 132-137 (1991)).

Modified antibodies, such as antibodies conjugated with a variety of molecules such as polyethylene glycol (PEG), may be used. In addition, the antibodies may be conjugated with a labeling substance, chemotherapeutic agent, cytotoxic substance such as a bacteria-derived toxin, etc. Labeled antibodies are particularly useful, and methods are known for labeling antibodies with enzymes, fluorescent substances, luminescent substances, radioisotopes, metal chelates, and such, and then detecting the labeled antibodies. A modified antibody may be obtained by directly applying chemical modification to the obtained antibody using a cross-linker and so on. Alternatively, an antibody may be conjugated with a low molecular weight hapten (for example, biotin, dinitrophenyl, pyridoxal, and fluorescamine), and indirectly labeled using a conjugate that recognizes the low molecular hapten. Moreover, antibodies whose sugar chains are modified may be used in the present invention. Techniques for modifying the sugar chains of antibodies are already known (for example, WO00/61739 and WO02/31140). An "antibody" in the present invention also comprises these antibodies.

If an antibody of the present invention is produced for use in cancer therapy, for example, one arm of the antibody may be prepared so as to recognize a tumor cell antigen, and the other arm may be designed to recognize a molecule that triggers cytotoxicity. Examples of tumor cell antigens include 1D10 (malignant B cell), AMOC-1 (pan carcinoma associated antigen), CAMA1, CD7, CD15, CD19, CD22, CD38, CEA, EGF receptor, Id-1, L-D1 (colon cancer), MoV18, p97, p185$^{HER2}$, OVCAR-3, neural cell adhesion molecule (NCAM), melanocyte-stimulating hormone analogue, and folate binding protein (FBP). Examples of cytotoxicity-triggering molecules are CD3, CD16, and FcγRI. In addition, a BsAb may be designed so that it can bind to a toxin such as IFN-α, saponin, vinca alkaloid, and ricin A chain.

Furthermore, an antibody of the present invention may be constructed so as to bind to a receptor that forms a heterodimer and changes the distance or angle between the chains or such upon ligand binding, thereby transducing signals inside the cell (for example, many cytokine receptors). The obtained antibody can be used as an agonist antibody that can mimic the ligand-induced dimerization of a receptor.

In addition to the above examples, the following antibodies are known: (1) antibodies that interact with an enzyme assisting conversion of chemical compounds, such as the conversion of mitomycin phosphate to mitomycin alcohol, (2) antibodies that bind to fibrin, tPA, uPA, or such, which are useful as fibrinogen dissolving agents, (3) antibodies that bind to LDL and Fc receptor (FcγRI, FcγRII, or FcγRIII) or such and direct immune complexes to cell surface receptors, (4) antibodies that recognize T cell antigens such as CD3 and antigens of pathogens such as HCV, Influenza, and HIV, which can be used for infectious diseases, (5) antibodies that bind to tumor antigens that can be used for tumor detection and detectable substances such as EOTUBE, DPTA, and hapten, (6) antibodies that can be used as vaccination adjuvants (Fanger et al. Crit. Rev. Immunol. 12: 101-124 (1992)), and (7) antibodies that recognize substances detectable for diagnosis (such as rabbit IgG, horseradish peroxidase (HRP), FITC, and β-galactosidase); and hormone, ferritin, somatostatin, substance P, CEA, and so on. The methods of the present invention can be used to produce a variety of antibodies, including the above described multi-specific antibodies (WO89/02922; EP314,317; and U.S. Pat. No. 5,116,964).

As described above, in the same way as conventional multi-specific antibodies, the antibodies of the present invention are useful for immunodiagnosis, therapies and diagnosis based on immunoassays in clinical fields and so on. An antibody of the present invention can be used for a variety of therapeutic purposes, for example: to trigger cytotoxicity such as killing tumor cells; to use as a vaccination adjuvant; to appropriately transport an agent such as a thrombolytic agent to an in vivo target; to precisely convert a pro-drug at a target site, where the pro-drug is activated by an enzyme; to direct an immune complex to a cell surface receptor for treating an infectious disease; and to transport an immunotoxin or such to a target cell such as a tumor cell.

Antibodies of the present invention can be formulated by methods known to those skilled in the art and used as pharmaceutical compositions. Such pharmaceutical compositions for therapeutic use, which comprise antibodies of the present invention, may be formulated by mixing as necessary with suitable pharmaceutically acceptable carriers, solvents and such that do not react with the antibodies. For example, sterilized water, saline, stabilizers, vehicles, antioxidants (e.g. ascorbic acid), buffers (e.g. phosphate, citrate, and other organic acids), preservatives, detergents (e.g. PEG and Tween), chelating agents (e.g. EDTA), and binders may be mixed. Furthermore, the pharmaceutical compositions may comprise other low molecular weight polypeptides, proteins such as serum albumin, gelatin and immunoglobulins, amino acids such as glycine, glutamine, asparagine, arginine, and lysine, carbohydrates and sugars such as polysaccharides and monosaccharides, and sugar alcohols such as mannitol and sorbitol. When prepared as an aqueous solution for injection, saline and isotonic solutions comprising glucose and other adjunctive agents such as D-sorbitol, D-mannose, D-mannitol, and sodium chloride may be used. In addition, appropriate solubilizing agents such as alcohols (e.g. ethanol), polyalcohols (e.g. propylene glycol and PEG), and non-ionic detergents (e.g. polysorbate 80 and HCO-50) may be used in combination.

If necessary, diabodies of the present invention may be encapsulated in microcapsules (microcapsules made of hydroxycellulose, gelatin, polymethylmethacrylate, and so on), and made into components of colloidal drug delivery systems (liposome, albumin microsphere, microemulsion, nano-particles, and nano-capsules) (see, for example, "Remington's Pharmaceutical Science 16th edition", Oslo Ed. (1980)). Moreover, methods are known for making sustained-release drugs, and these can be applied to the diabodies of the present invention (Langer et al., J. Biomed. Mater. Res. 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP 133,988).

Patients can be administered with the antibodies by any route, either oral or parenteral, but preferably by a parenteral route. Specifically, administration is performed by injection, nasally, transpulmonarily, subcutaneously, etc. For example, the antibodies may be administered by injection systemically or locally via intravenous injection, intramuscular injection, intraperitoneal injection, subcutaneous injection, and so on. In addition, an appropriate administration method may be selected based on the age or symptoms of a patient. A dose may be selected, for example, within the range of 0.0001 mg to 1,000 mg per kg body weight. Alternatively, a dose may be selected, for example, within the range of 0.001 mg to 100,000 mg/body. However, the present invention is not limited to these above-described doses and administration methods.

The antibodies of the present invention may be used for enzyme immunoassays. For this purpose, one of the antibody variable regions of an antibody is designed to recognize an epitope that does not interfere with the enzymatic activity of the enzyme, and the other region is designed to recognize a carrier that binds to the antibody. For example, antibodies that recognize IgG, ferritin, HRP, and hormones may be used for such assays.

In addition, the antibodies of the present invention may be used for in vivo and in vitro immunodiagnosis of a variety of diseases. For example, the variable region of one pair of an antibody can be designed to recognize an antigen that is specific to tumor cells, and the other can be designed to bind a detectable marker. Detectable markers include radioisotopes (e.g. $^3$H, $^{14}$C, $^{32}$P, $^{35}$S, and $^{125}$I), fluorescent dyes (e.g. fluorescein and luciferin), chemiluminescent compounds (e.g. isothiocyanate and rhodamine), and generally used enzymes such as alkaline phosphatase, β-galactosidase, and HRP. The binding of antibodies to these substances and detection of such can be performed according to known methods (Hunter et al., Nature 144: 945 (1962); David et al., Biochemistry 13: 1014 (1974); Pain et al., J. Immunol. Meth. 40: 219 (1981); Nygen, J. Histochem. Cytochem. 30: 407 (1982)). The antibodies of the present invention which are capable of reacting with such detectable substances can also be used in a variety of assays, including competitive binding assays, direct and indirect sandwich immunoassays (e.g. ELISA), and immunoprecipitation assays (Zola, "Monoclonal Antibodies: A Manual of Techniques", 147-158, CRC Press Inc. (1987)).

If the antibodies of the present invention are used for the above-described diagnosis or such, the antibodies may be bound to insoluble carriers as necessary. Methods for binding antibodies to insoluble carriers are well known, and commonly used chemical coupling methods or physical absorption may be used to immobilize antibodies. Examples of insoluble carriers include those with desired forms, such as spherical, fibrous, rod, container (such as a tray), disc, cell and test tube forms, which are made of a variety of synthetic resins, polysaccharides, glasses, metals, and so on.

3. Antibody Compositions

In the present invention, the term "antibody composition" means a group comprising multiple kinds of antibodies.

"Increasing the proportion of a desired antibody in an antibody composition" means increasing the proportion of an antibody made of the first and second pairs in the antibody composition. Thus, it means decreasing the proportion of antibodies that comprise a pair formed from the first H chain and second L chain, or a pair formed from the second H chain and first L chain. Therefore, the antibody compositions of the present invention generally have increased specific activities.

Indices for the specific activity of an antibody include its binding activity, agonist activity, antagonist activity, and neutralizing activity. An index detected to measure the specific activity may be any index, as long as it enables the measurement of a quantitative and/or qualitative change in the desired antibody in an antibody composition. For example, indices used for cell-free assays, cell-based assays, tissue-based assays, and in vivo assays may be used. The indices for cell-free assays may be enzyme reactions based on a present antibody's binding activity, agonist activity, antagonist activity, neutralizing activity and such; or a quantitative and/or qualitative change in a protein, DNA, and RNA. Examples of enzyme reactions include reactions such as amino acid transfer, glycosyltransfer, dehydration, dehydrogenation, and substrate cleavage. Other indices that may be used include protein phosphorylation, dephosphorylation, dimerization, multimerization, degradation, dissociation and such; and DNA or RNA amplification, cleavage, and extension. In addition, phosphorylation of proteins located downstream of a signal transduction pathway may be detected as an index. Indices used in cell-based assays may be changes in cell phenotype due to a present antibody's binding activity, agonist activity, antagonist activity, neutralizing activity and such. Examples of such changes include quantitative and/or qualitative changes in a product, changes in proliferation activity, cell shape changes, and changes in characteristics. The products may be secreted proteins, cell surface antigens, intracellular proteins, mRNAs or such. Shape changes include a process formation and/or change in the number of processes, changes in flatness, the degree of extension/aspect ratio, cell size, intracellular structures, heterogeneity/homogeneity of cell population, and changes in cell density. Such cell shape changes are normally confirmed by observation under a microscope. Changes in characteristics include changes in anchorage dependency, cytokine-dependent responses, hormone dependency, drug resistance, cell motility, cell migratory activity, beating, and intracellular substances. Cell motility includes cell invasion activity, and cell migration activity. Changes to intracellular substances may be changes in enzyme activities, mRNA levels, the levels of intracellular messengers such as $Ca^{2+}$ and cAMP, cellular protein levels, etc. Changes in cell proliferation activity, induced by binding to a receptor, agonist effect, antagonist effect, or neutralizing effect of the antibody of the present invention, may be used as an index. Indices for detection in tissue-based assays may be functional changes corresponding to the tissues being used. Indices for in vivo assays include changes in tissue weight, changes in the blood system such as the number of hematopoietic cells, changes in protein level, enzyme activity, and electrolyte level; or changes in the circulation system such as blood pressure and cardiac rate, which are caused by the binding, agonist activity, antagonist activity, neutralizing effect or such of an antibody of the present invention.

The methods for measuring these detection indices are not particularly limited; and luminescence, color development, fluorescence, radioactivity, fluorescence polarization, surface plasmon resonance signal, time-resolved fluorescence, mass, absorbance spectrum, light scattering, fluorescence resonance energy transfer and such may be used. These methods of measurement are well known to those skilled in the art, and may be appropriately selected depending on the purpose. For example, absorbance spectra can be determined using a commonly used photometer, plate reader or such; luminescence can be measured using a luminometer or the like; and fluorescence can be measured with a fluorometer or such. Mass can be measured using a mass spectrometer. Radioactivity can be determined using a measuring device depending on the type of radiation, such as a gamma counter. Fluorescence polarization can be measured using BEACON (TaKaRa Shuzo); surface plasmon resonance signals can be measured using BIACORE, and time-resolved fluorescence and fluorescence resonance energy transfer can be measured with ARVO and so on. In addition, a flow cytometer and such may be used. In these measuring methods, two or more detection indices may be measured for a single method. Furthermore, two or more measurements can be performed simultaneously and/or continuously to measure multiple detection indices, if convenient. For example, fluorescence and fluorescence resonance energy transfer can be simultaneously measured using a fluorometer.

4. Vectors and Cells

The present invention provides vectors in which the expression of antibody H or L chains is induced using an expression inducing agent, which can be used in the methods of producing antibodies of this invention. The vectors used in such methods are preferably vectors in which the expression of both the H chain and L chain forming a pair is induced by a single expression regulator. In this case, the genes encoding the H chain and L chain may be integrated in the same single vector, or in separate vectors. In addition, the present invention relates to vector kits comprising a vector encoding the first L chain and first H chain, and a vector encoding the second L chain and second H chain. In the vector kits, expression of the first L chain and first H chain is preferably induced by an expression regulator different from that inducing expression of the second L chain and second H chain. Furthermore, if necessary, the vectors and vector kits of the present invention may be constructed so that expressions of the first H chain, first L chain, second H chain, and second L chain are respectively induced with different expression regulators.

The present invention provides cells comprising the above vectors or vector kits. Preferably, the cells can express a pair of the first H chain and first L chain of an antibody, and a pair of the second H chain and second L chain at different times. The vectors and cells of the present invention are specifically described in the above section of "1. Methods for producing antibodies".

Any prior publications cited herein are incorporated by reference.

BEST MODE FOR CARRYING OUT THE INVENTION

Hereinbelow, the present invention will be specifically described using Examples, however, it is not to be construed as being limited thereto.

Example 1

Construction of Expression Plasmids for a Bispecific IgG Antibody that can Bind to Human IFN Heteroreceptor (AR1/AR2)

When only one of the light chains of an anti-AR1 or anti-AR2 antibody is expressed along with two H chains, and is shared by the H chains, the resulting antibody loses activity and may function as an inhibitor instead. Therefore, when both L chains are expressed and an IgG of a desired combination is preferentially expressed, the apparent specific activity of IgG is expected to increase.

When producing bispecific IgG antibodies, amino acids in the CH3 domain of human IgG4 were substituted based on the knob-into-hole techniques used for IgG1 (Ridway et al., Protein Eng. 9(61): 7-21 (1996)) so that molecules with a heterologous H chain combination were formed. The "type a" substitution product (human IgG4γa) carries Y349C and T366W substitutions, and "type b" (human IgG4γb) carries E356C, T366S, L368A, and Y407V substitutions. In addition, a substitution (-ppcpScp- to -ppcpPcp-) was introduced to the hinge regions of both derivatives.

The tetracycline inducible vector pcDNA4 (Invitrogen) was used to express one arm of an antibody molecule against an AR1 receptor (for convenience referred to as the right arm HL molecule). Vectors (pcDNA1-24H or pcDNA1-24L) were constructed as is known in the art, such that they contained expression units for the respective H and L chains composing the right arm HL molecule, in which the variable region ($V_H$ or $V_L$) of a mouse antibody recognizing AR1 receptor, and the constant region of human IgG4γa or the human κ constant region were incorporated, respectively, downstream of the signal sequence for animal cells (IL3ss) (Proc. Natl. Acad. Sci. U.S.A. 81: 1075 (1984)).

An ecdysone analogue-inducible vector pIND (Invitrogen) was used to express the other arm of the antibody molecule recognizing AR2 receptor (referred to as the left arm HL molecule, for convenience). Vectors containing expression units for the respective H and L chains composing the left arm HL molecule of the antibody were similarly constructed (pIND2-7H or pIND2-7L), in which the variable region ($V_H$ or $V_L$) of a mouse antibody recognizing AR2 receptor, and the constant region of human IgG4γb or the human κ constant region were incorporated, respectively, downstream of the signal sequence for animal cells (IL6ss) (EMBO J. 6: 2939 (1987)). The plasmid DNAs were isolated using a commercially available plasmid purification kit (QIAprep Spin Miniprep kit, QIAGEN). Plasmids were stored at 4° C. until use.

Example 2

Preparation of Bispecific IgG Antibodies by Temporal Differential Expressions of HL Molecules in Animal Cells

2-1. Preparation of DNA

The expression vectors (pcDNA1-24H and pcDNA1-24L) for the right arm HL molecule of the antibody can be induced by tetracycline. In order to completely suppress their expression in the absence of tetracycline, the plasmid pcDNA6/TR (Invitrogen) encoding the Tet repressor (TetR) is required. TetR forms a dimer, which binds to the two Tet operator sequences (TetO2) on pcDNA4/TO and suppresses transcription of a desired gene. Once tetracycline is added, it binds to the TetR dimer and causes conformational changes, which release TetR from the Tet operator and then transcription of the desired gene is induced by the CMV/TetO2 promoter. On the other hand, the expression vectors (pIND2-7H and pIND2-7L) for the left arm HL molecule of the antibody can be induced by an analogue compound of the insect hormone ecdysone (muristerone A or ponasterone A). This system requires plasmid pVgRXR (Invitrogen) that constitutively expresses the ecdysone receptor and retinoid X receptor, which react with an ecdysone analogue compound and induce expression. Following the addition of an ecdysone analogue compound, the analogue compound, a heterodimer of ecdysone receptor, and retinoid X receptor bind to the ecdysone/glucocorticoid promoter (5XE/GRE), and activate the expression of a desired gene. Thus, a solution containing a mixture of six kinds of plasmid DNA, comprising pcDNA1-24H, pcDNA1-24L, pIND2-7H, pIND2-7L, pcDNA6/TR, and pVgRXR, was prepared for transfection into animal cells.

2-2. Transfection of Animal Cells

When COS-7 cells (Invitrogen) which are derived from the cultured cell line of African green monkey kidney were used, the cells were suspended in DMEM medium supplemented with 10% FCS, plated into each well of 6-well plates for adherent cells (CORNING) at a cell density of $1 \times 10^5$ cells/ml, 1 ml per well, and then cultured overnight at 37° C., 5% CO2 in an incubator. The plasmid solution prepared in Section 2-1 was added to a mixture of 1.5 μl of FuGENE6 transfection reagent (Roche) (Invitrogen) and 250 μl of Opti-MEM I medium (Invitrogen), left for 20 minutes at room temperature, and added to the cells in each well. The culture was incubated for four to five hours at 37° C., 5% CO2 in an incubator.

When HEK293H cells (Invitrogen) which are derived from the cell line of human embryonic kidney were used, the cells were suspended in DMEM medium supplemented with 10% FCS, plated into each well of 12-well plates for adherent cells (CORNING) at a cell density of $5 \times 10^5$ cells/ml, 1 ml per well, and then cultured overnight at 37° C., 5% $CO_2$ in a incubator. The plasmid solution prepared in Section 2-1 was added to a mixture of 7 μl of Lipofectamine 2000 transfection reagent (Invitrogen) and 250 μl of Opti-MEM I medium (Invitrogen), left for 20 minutes at room temperature, and then added to the cells in each well. The culture was incubated for four to five hours at 37° C., 5% $CO_2$ in an incubator.

2-3. Inducible Expression of Bispecific IgG Antibody

The culture medium was removed by aspiration from the cell culture transfected in Section 2-2. The culture was replenished with 1 ml of CHO-S-SFM-II (Invitrogen) containing 1 μg/ml of tetracycline hydrochloride (WAKO Chemical), and incubated for one day at 37° C., 5% $CO_2$ in an incubator to perform the first inducible expression of the right arm HL molecule of the antibody. The culture medium was removed by aspiration, and the culture was washed once with 1 ml of CHO-S-SFM-II medium, 1 ml of the same medium containing 5 μM of muristerone A (Invitrogen) or ponasterone A (Invitrogen) was added thereto, and incubated for two or three days at 37° C., 5% $CO_2$ in an incubator to perform the secondary induction of expression of the left arm HL molecule of the antibody, and to secrete a bispecific IgG antibody into the medium. The culture supernatant was collected, centrifuged once at about 2,000×g at room temperature for five minutes to remove the cells, and concentrated as necessary using Microcon-50 (Millipore). The sample was stored at 4° C. until use.

2-4. Purification of the Expressed Antibody

The culture supernatant sample as prepared in Section 2-3 was purified using Protein A resin (rmp Protein A Sepharose FAST FLOW, Amersham Biosciences). Specifically, 50 µl of the resin previously equilibrated with TBS buffer was added to 4 ml of the supernatant, and mixed by continuous inversion at 4° C. overnight to absorb the antibody onto the resin. After the mixture was centrifuged at 3,000×g for 10 minutes to remove the supernatant, the resin was resuspended with 500 µl of TBS buffer, and transferred onto a 0.22 µm filter cup (Millipore). A cycle of centrifugation at 3,000×g for one minute and washing with TBS buffer was then repeated three times. 100 µl of elution buffer (10 mM HCl, 150 mM NaCl, 0.01% Tween-20) was used for elution. 5 µl of 1 M Tris solution containing 150 mM NaCl was added to the eluate to neutralize it. The solution was stored at 4° C. until use.

2-5. Quantitation of Human IgG

A goat affinity purified antibody to human IgG Fc (Cappel) was diluted at 1 µg/ml with coating buffer and immobilized onto 96-well MaxiSorp Surface Immunoplates (NALGE NUNC International). The plates were blocked with Diluent buffer (D.B.), and the culture supernatant or purified antibody, which is appropriately diluted with D.B., were added thereto as a sample. In addition, ChromPure Human IgG, whole molecule (Jackson ImmunoResearch, 11.1 mg/ml) was diluted with D.B. into eleven samples using two-fold dilutions starting from 1,000 ng/ml and these were added as the standard for calculating antibody concentration. After washing three times, the plates were reacted with a goat anti-human IgG, alkaline phosphatase (Biosource). After washing five times, the signals were developed using Sigma 104® phosphatase substrate (Sigma Chemical), and absorbance at 405 nm with the reference wavelength 655 nm was measured using the absorbance reader Model 1550 (Bio-Rad Laboratories). The human IgG concentration in the culture supernatant was calculated from the standard curve using the software Microplate Manager III (Bio-Rad Laboratories).

Example 3

Measurement of Human IFN Agonist Activity by a Reporter Gene Assay

The IFN agonist activity (relative luciferase unit: RLU) of the non-purified antibody was examined using transformant cells that were a human hepatoma derived HuH-7 cell line (National Institute of Health Sciences, Japan) introduced with the plasmid pISRE-Luc (Stratagene), which carries the luciferase gene downstream of an element responsive to IFN stimulus. The activity was measured according to the instructions described in the manual accompanying the luciferase quantitation system Bright-Glo™ Luciferase Assay System (Promega). Human IFNα (rhIFN-αA, Calbiochem) was used as a positive control. The results are shown in FIG. 1. Samples with expressions induced using the inducible vectors at different times (3-3, 4-4, 5-3, and 7-4) had specific activities increased by 5- to 10-fold compared to samples with expression induced by the inducible vectors simultaneously (2-3). Thus, the results strongly suggest that expressing HL molecules at different times leads to the reduction of the proportion of IgG with undesired combinations, and thereby increases specific activity.

Example 4

Analysis of the Expression Level of a Desired Antibody Using Sandwich ELISA

Each His-tagged receptor (AR1-His or AR2-His) was diluted with Diluent buffer (D.B.) to 500 ng/ml, and 100 µl of each was added to the wells of a 96-well Ni-NTA HisSorb Plate (QIAGEN), and absorbed at 4° C. overnight. Supernatant was removed by aspiration, then 200 µl of SuperBlock™ Blocking Buffer in TBS (PIERCE) was added thereto, and blocking was performed 60 minutes at room temperature. After washing three times, purified antibodies diluted with D.B (31.25 to 500 ng/ml) were added, and incubated at room temperature for 60 minutes. One antibody sample was expressed by simultaneous induction with tetracycline and ponasterone A after transfection (simultaneous induction), and the other was expressed by induction with tetracycline for one day followed by induction with ponasterone A for two days (temporal differential expression). After three washes, 100 µl of biotinylated secondary antibody corresponding to the respective antibodies (that is, AR2-biotin for AR1-His, and AR1-biotin for AR2-His) diluted with D.B. to 500 ng/ml was added to the plate, and incubated at room temperature for 60 minutes. After five washes, the signals were developed using Sigma 104® phosphatase substrate (Sigma Chemical), and absorbance at 405 nm with reference wavelength 655 nm was measured using the absorbance reader Model 1550 (Bio-Rad Laboratories).

In both kinds of ELISA strategies (AR1-His+Antibody+AR2-biotin, and AR2-His+Antibody+AR1-biotin), the samples in which expression of each HL molecule was induced at different times showed about a twofold higher binding ability per unit antibody level than samples in which both HL molecules were expressed simultaneously. This result indicates the preferential proportion of the desired type among the expressed IgGs.

INDUSTRIAL APPLICABILITY

The present invention provides methods for preferentially producing a desired antibody when producing multi-specific antibodies which bind to multiple antibodies or antibody fragments. More specifically, when producing bispecific antibodies (BsAbs), for example, the methods of the present invention can be used to efficiently produce a desired BsAb by inhibiting contact between the first light chain and second heavy chain, which are not linked with the first heavy chain and second light chain respectively, and contact between the first heavy chain and second light chain, which are not linked with the first light chain and second heavy chain respectively. Thus, the methods for producing multi-specific antibodies of the present invention enable an increase in the proportion of an antibody composed of the correct pairs of heavy and light chains in the antibody compositions produced, and an increase in the specific activity of multi-specific antibodies useful for immunodiagnosis, therapy, diagnosis using immunoassays, and such in clinical fields.

The invention claimed is:

1. A method for producing an antibody, wherein the method comprises
(a) providing a recombinant eukaryotic host cell comprising exogenous nucleic acid encoding a first light chain downstream of a signal sequence and exogenous nucleic acid encoding a first heavy chain downstream of a signal sequence and exogenous nucleic acid encoding a second light chain downstream of a signal sequence and exogenous nucleic acid encoding a second heavy chain downstream of a signal sequence, wherein the amino acid sequences of the first heavy chain and the second heavy chain are different, and the amino acid sequences of the first light chain and the second light chain are different, and wherein the CH3 domain of one of the first and second heavy chains carries one or more amino acid substitutions, and the CH3 domain of the other heavy chain carries one or more different amino acid substitutions, wherein the substitutions permit the first and second heavy chains to pair together into a knobs-into-holes structure, and wherein expression of the first light chain and the first heavy chain is induced by a first exogenous expression regulator, expression of the second light chain and the second heavy chain is induced by a second exogenous expression regulator, and the first and the second exogenous expression regulators are different;
   (b) inducing expression of the first light chain and first heavy chain in the cell;
   (c) causing induction of expression of the first light chain and first heavy chain to cease;
   (d) subsequent to step (c), inducing expression of the second light chain and second heavy chain in the cell, such that expression of the first light chain and first heavy chain is temporally separate from expression of the second light chain and second heavy chain in the cell; and
   (e) isolating a four-chain antibody comprising the first light and heavy chains and the second light and heavy chains, wherein the four-chain antibody is a bispecific antibody, wherein the first light chain and the first heavy chain together recognize a first antigen, and the second light chain and the second heavy chain together recognize a second antigen.

2. The method of claim 1, wherein each of the first light chain, the first heavy chain, the second light chain and the second heavy chain is encoded on a separate vector.

3. The method of claim 1, wherein the first light and heavy chains are encoded on a first vector and the second light and heavy chains are encoded on a second vector.

4. The method of claim 1, wherein the first light chain, the first heavy chain, the second light chain and the second heavy chain are all encoded on a single vector.

5. The method of claim 1, wherein one of the expression regulators is tetracycline, ecdysone, muristerone A, or ponasterone A.

6. A method for producing an antibody, the method comprising:
   (a) providing a recombinant eukaryotic host cell containing (i) exogenous nucleic acid encoding a first light chain downstream of a signal sequence and exogenous nucleic acid encoding a first heavy chain downstream of a signal sequence, wherein the first light and heavy chains bind to a first antigen, and (ii) exogenous nucleic acid encoding a second light chain downstream of a signal sequence and exogenous nucleic acid encoding a second heavy chain downstream of a signal sequence, wherein the second light and heavy chains bind to a second antigen, wherein the amino acid sequences of the first heavy chain and second heavy chain are different and the amino acid sequences of the first light chain and the second light chain are different, wherein the expression of the first light chain and the first heavy chain is induced by a first exogenous expression regulator, expression of the second light chain and the second heavy chain is induced by a second exogenous expression regulator, and the first and the second exogenous expression regulators are different, and wherein the CH3 domain of one of the first and second heavy chains carries one or more amino acid substitutions, and the CH3 domain of the other heavy chain carries one or more different amino acid substitutions, wherein the substitutions permit the first and second heavy chains to pair together into a knobs-into-holes structure;
   (b) inducing expression of the first light and heavy chains;
   (c) following expression of the first light and heavy chains, causing the induction of expression of the first light and heavy chains to cease;
   (d) subsequent to step (c), inducing expression of the second light and heavy chains, such that expression of the first light chain and first heavy chain is temporally separate from expression of the second light chain and second heavy chain in the cell; and
   (e) isolating a four-chain, bispecific antibody that binds to both the first antigen and the second antigen, wherein the four-chain, bispecific antibody comprises the first light and heavy chains and the second light and heavy chains.

7. The method of claim 1, wherein the eukaryotic cell is an animal cell.

8. The method of claim 7, wherein the animal cell is a mammalian cell.

9. The method of claim 6, wherein the eukaryotic cell is an animal cell.

10. The method of claim 9, wherein the animal cell is a mammalian cell.

11. The method of claim 8, wherein the mammalian cell is a COS-7 cell or a HEK293 cell.

12. The method of claim 10, wherein the mammalian cell is a COS-7 cell or a HEK293 cell.

13. The method of claim 1, wherein the CH3 domain of one of the first and second heavy chains carries Y349C and T366W substitutions, and the CH3 domain of the other heavy chain carries E356C, T366S, L368A, and Y407V substitutions.

14. The method of claim 6, wherein the CH3 domain of one of the first and second heavy chains carries Y349C and T366W substitutions, and the CH3 domain of the other heavy chain carries E356C, T366S, L368A, and Y407V substitutions.

* * * * *